(12) United States Patent
Danley

(10) Patent No.: US 6,561,692 B2
(45) Date of Patent: May 13, 2003

(54) DIFFERENTIAL SCANNING CALORIMETER

(75) Inventor: Robert L. Danley, Collingswood, NJ (US)

(73) Assignee: TA Instruments-Waters LLC, New Castle, DE (US)

(*) Notice: Subject to any disclaimer, the term of this patent is extended or adjusted under 35 U.S.C. 154(b) by 0 days.

(21) Appl. No.: 09/769,313

(22) Filed: Jan. 26, 2001

(65) Prior Publication Data
US 2003/0072348 A1 Apr. 17, 2003

Related U.S. Application Data

(63) Continuation-in-part of application No. 09/533,949, filed on Mar. 23, 2000, now abandoned, and a continuation-in-part of application No. 09/643,870, filed on Aug. 23, 2000, now Pat. No. 6,431,747, and a continuation-in-part of application No. 09/643,869, filed on Aug. 23, 2000, now Pat. No. 6,428,203.
(60) Provisional application No. 60/226,904, filed on Aug. 23, 2000, and provisional application No. 60/226,905, filed on Aug. 23, 2000.

(51) Int. Cl.[7] .......... G01N 1/00; G01N 25/00; G01K 1/20; G01K 17/04; G01K 17/08
(52) U.S. Cl. .......... 374/29; 374/31; 374/10; 374/1; 374/32; 374/33
(58) Field of Search .......... 374/10–11, 29–32, 374/33–43, 12–13

(56) References Cited

U.S. PATENT DOCUMENTS

| 3,263,484 A | 8/1966 | Watson et al. |
| 3,732,722 A | 5/1973 | Norem et al. |
| 4,095,453 A | 6/1978 | Woo |

(List continued on next page.)

FOREIGN PATENT DOCUMENTS

| DE | 30 49 105 A | 7/1982 |
| DE | 3049 105 A | 7/1982 |
| EP | 0 701 122 | 3/1996 |
| WO | WO 95/33199 | 7/1995 |
| WO | WO 95 33199 | 12/1995 |
| WO | WO 98 20314 A | 5/1998 |

OTHER PUBLICATIONS

"High Precision Heat Capacity Measurement by Dynamic Differential Scanning Calorimetry," Hatta, et al., Jpn. J. Appl. Phys., vol. 35, L858–860 (1996), chapters 2–3.

"Diagnosis of Phase Shift in a Temperature–Modulated Calorimetric Method," HATTA et al., Journal of Thermal Analysis., vol. 4, pp. 577–584 (1998).

"A Differential Scanning Calorimeter for Quantitative Differential Thermal Analysis," E.S. Watson and M.J. O'Neill, Analytical Chemistry, vol. 36, No. 7, pp. 1233–1238 (Jun. 1994).

"Differential Scanning Calorimetry an Introduction for Practitioners," G. Hohne, W. Hemminger and H.J. Flammersheim (Springer–Verlag, 1996).

(List continued on next page.)

*Primary Examiner*—Diego Gutierrez
*Assistant Examiner*—Gail Verbitsky
(74) *Attorney, Agent, or Firm*—Shaw Pittman LLP

(57) ABSTRACT

A modulated differential scanning calorimeter (MDSC) and a method for practicing MDSC that uses two separate temperature difference signals—the difference between the temperatures of the sample and reference positions and the difference between the temperatures of the sample position and a base position. This approach accounts for heat flows associated with the sample and reference pans, and for the difference in sample and pan heating rates to provide more accurate heat flow measurement and improve resolution. It also greatly reduces or eliminates the frequency dependence of the heat capacity calibration factor, which allows for the use of shorter modulation periods. Shorter modulation periods allow the use of higher underlying heating rates, allowing users to decrease the duration of their MDSC experiments.

38 Claims, 11 Drawing Sheets

U.S. PATENT DOCUMENTS

| | | |
|---|---|---|
| 4,330,933 A | 5/1982 | Bullinger et al. |
| 4,350,466 A | 9/1982 | Bahr et al. |
| 4,530,608 A | 7/1985 | O'Neill |
| 4,614,721 A | 9/1986 | Goldberg |
| 4,783,174 A | 11/1988 | Gmelin et al. |
| 4,812,051 A | 3/1989 | Paulik et al. |
| 5,033,866 A | 7/1991 | Kehl et al. |
| 5,211,477 A | 5/1993 | Li |
| 5,224,775 A | 7/1993 | Reading et al. |
| 5,288,147 A | 2/1994 | Schaefer et al. |
| 5,599,104 A | 2/1997 | Nakamura et al. |
| 5,672,289 A | 9/1997 | O'Neill |
| 5,813,763 A | 9/1998 | Plotnikov et al. |
| 5,842,788 A | 12/1998 | Danley et al. |
| 6,079,873 A | 6/2000 | Cavicchi et al. |
| 6,146,012 A | 11/2000 | Nakamura et al. |
| 6,170,984 B1 | 1/2001 | Schawe et al. |
| 6,200,022 B1 | 3/2001 | Hammiche et al. |
| 6,390,669 B1 | 5/2002 | Nakamura et al. |

OTHER PUBLICATIONS

"Heat Capacity by Multi–Frequencies Sawtooth Modulation," B. Wunderlich, R. Androsch, M. Pyda and Y.K. Kwon, submitted to Thermochimica Acta, Sep. 1999.

"Heat Capacity Measurement by Modulated DSC at Constant Temperature," A. Boller, Y. Jin, B. Wunderlich, Journal of Thermal Analysis, vol. 42 (1994), pp. 307–330.

"The Anaysis of Temperature Controlled Scanning Calorimeter," M.J. O'Neill, Analytical Chemistry, vol. 36, No. 7, pp. 1238–1245 (Jun. 1994).

DIFFERENTIAL SCANNING CALORIMETER

The present application claims priority from the Aug. 23, 2000 filing date of U.S. Provisional Patent Applications Nos. 60/226,904 and 60/226,905. The present application is a continuation-in-part application of U.S. patent application Ser. No. 09/533,949 (the "'949 application"), filed Mar. 23, 2000 now abandoned, which is incorporated herein by reference, U.S. patent application Ser. No. 09/643,870, entitled "Heat Flux Differential Scanning Calorimeter," filed Aug. 23, 2000 now U.S. Pat. No. 6,431,747, which is also incorporated by reference herein, and U.S. patent application Ser. No. 09/643,869 (the "'869 application"), entitled "Power Compensation Differential Scanning Calorimeter," filed Aug. 23, 2000 now U.S. Pat. No. 6,428,203, which is also incorporated by reference herein.

BACKGROUND

Differential Scanning Calorimeters measure the heat flow to a sample as the sample temperature is varied in a controlled manner. There are two basic types of DSCs, heat flux and power compensation. Brief descriptions of the two types of DSC are included below. A detailed description of the construction and theory of DSCs is disclosed in "Differential Scanning Calorimetry an Introduction for Practitioners", G. Höhne, W. Hemminger and H.-J. Flammersheim (Springer-Verlag, 1996).

Heat flux DSCs include a sensor to measure heat flow to a sample to be analyzed. The sensor has a sample position and a reference position. The sensor is installed in an oven whose temperature is varied dynamically according to a desired temperature program. As the oven is heated or cooled, the temperature difference between the sample and reference positions of the sensor is measured. This temperature difference is assumed to be proportional to the heat flow to the sample.

Power compensation DSCs include a sample and a reference holder installed in a constant temperature enclosure. Each of the holders has a heater and a temperature sensor. The average of the sample and reference holder temperatures is used to control temperature, which follows the desired temperature program. In addition, differential power proportional to the temperature difference between the holders is added to the average power to the sample holder and subtracted from the average power to the reference holder in an effort to reduce the temperature difference between sample and reference holders to zero. The differential power is assumed to be proportional to the sample heat flow and is obtained by measuring the temperature difference between the sample and reference holder. In commercial power compensation DSCs, the difference between sample and reference temperature is generally not zero because a proportional controller is used to control the differential power.

Modulated DSC (MDSC) is a technique for measuring heat flow in a Differential Scanning Calorimeter in which the DSC is subjected to periodic temperature oscillations superimposed on the constant heating rate segments of conventional DSC. MDSC is described in U.S. Pat. No. 5,224,775, which is incorporated herein by reference. In a preferred embodiment, the resultant oscillating sample heat flow signal is separated into reversing and nonreversing components. The current MDSC heat flow measurement requires an increasingly large heat capacity calibration factor to obtain correct results as the modulation period decreases. This frequency dependence limits applicability to relatively long periods. The present invention is an MDSC method that eliminates, or greatly reduces the frequency dependence. This reduces uncertainty in heat capacity and in the reversing and nonreversing heat flow signals. It also increases productivity by allowing the user to use shorter periods and, consequently, higher underlying heating rates.

To carry out a measurement on a DSC, the sample to be analyzed is loaded into a pan and placed on the sample position of the DSC. An inert reference material may be loaded into a pan and placed on the reference position of the DSC, although usually the reference pan is empty. The temperature program for conventional DSCs typically includes combinations of linear temperature ramps and constant temperature segments. Modulated DSC uses a temperature program in which periodic temperature oscillations are superposed on linear ramps and isothermal segments. The experimental result is the sample heat flow versus temperature or time. The heat flow signal is the result of heat flow to or from the sample due to its specific heat and as a result of transitions occurring in the sample.

During the dynamic portion of the DSC experiment, a temperature difference is created between the sample and reference positions of the DSC. In heat flux DSCs, the temperature difference results from the combination of three differential heat flows: the difference between the sample and reference heat flow, the difference between sample and reference sensor heat flow and the difference between sample and reference pan heat flow. In power compensation DSCs, the temperature difference results from the combination of three differential heat flows plus the differential power supplied to the sample holders: the difference between the sample and reference heat flow, the difference between sample and reference holder heat flow and the difference between sample and reference pan heat flow. The heat flow difference between the sample and reference consists of heat flow due to the heat capacity difference between the sample and reference, the heat flow of a transition, or the difference in heating rate that occurs during an MDSC experiment. The heat flow difference between the sample and reference sections of the DSC is the result of thermal resistance and capacitance imbalances in the sensor or between the holders and the difference in heating rate that occurs between the sample and reference sections of the DSC during a transition or during an MDSC experiment. Similarly, the heat flow difference between the sample and reference pans is the result of mass differences between the pans and the difference in heating rate that occurs during a sample transition or during a MDSC experiment.

In conventional heat flux DSCs the sensor imbalance and pan imbalance are assumed to be insignificant and the differences in heating rates are ignored. In conventional power compensation DSCs the holder imbalance and pan imbalance are assumed to be insignificant and the differences in heating rates are ignored. When the balance assumptions are satisfied and the sample heating rate is the same as the programmed heating rate, the temperature difference is proportional to the sample heat flow and the differential temperature gives an accurate measure of the sample heat flow. The sample heat flow is only proportional to the measured temperature difference between sample and reference when the heating rate of the sample and reference are identical, the sensor is perfectly symmetrical, and the pan masses are identical. Proportionality of sample heat flow to temperature difference for a balanced sensor and pans occurs only during portions of the experiment when the instrument is operating at a constant heating rate, the sample is changing temperature at the same rate as the instrument and there are no transitions occurring in the sample. During Modulated DSC experiments, the heating rates of the sample and reference are generally not the same and the difference between measured sample and reference temperatures is not proportional to the sample heat flow.

Thus, the sample heat flow from a conventional DSC is not the actual sample heat flow, but includes the effects of imbalances and differences in heating rates; in other words the DSC sample heat flow measurement is smeared. For many DSC experiments, the smeared sample heat flow is a sufficiently accurate result. For example, when the desired experimental result is the total energy of the transition, such as the heat of fusion of a melt, the total peak area is integrated over a suitable baseline and the result from a conventional DSC is sufficiently accurate. If however, partial integration of the peak area is required (for example, in the study of reaction kinetics), the smeared sample heat flow of conventional DSC cannot be used. Another example of when the conventional DSC result is inadequate is when two or more transitions in a sample occur within a small temperature interval. In that case, the transitions may be poorly separated in prior art DSCs because of the smearing effects. The improvement in resolution of the present invention greatly improves the separation of closely spaced transitions. In any case, the heat flow signal from prior art DSCs does not accurately portray the sample heat flow during a transition.

During a transition, the heat flow to the sample increases or decreases from the pre-transition value depending upon whether the transition is exothermic or endothermic and whether the DSC is being heated or cooled. The change in sample heat flow causes the heating rate of the sample to be different from that of the DSC and as a consequence, the sample pan and sensor heating rates become different from the programmed heating rate.

U.S. patent applications Ser. Nos. 09/533,949 and 09/643,870, incorporated by reference above, disclose a heat flux DSC that uses a four term heat flow equation to account for sensor imbalances and differences in heating rate between the sample and reference sections of the sensor. The four term DSC heat flow equation derived in the '949 application is:

$$q = \Delta T_0 \cdot \left(\frac{R_r - R_s}{R_r \cdot R_s}\right) - \frac{\Delta T}{R_r} + (C_r - C_s) \cdot \frac{dT_s}{d\tau} - C_r \cdot \frac{d\Delta T}{d\tau}$$

The first term accounts for the effect of the difference between the sensor sample thermal resistance and the sensor reference thermal resistance. The second term is the conventional DSC heat flow. The third term accounts for the effect of the difference between the sensor sample thermal capacitance and the sensor reference thermal capacitance. The fourth term accounts for the effect of the difference between the heating rates of the sample and reference sides of the DSC.

U.S. patent application Ser.No. 09/643,869, incorporated by reference above, discloses a power compensation DSC that uses a five term heat flow equation to account for sample and reference holder imbalances and differences in heating rate between the sample and reference holders. The five term power compensation DSC heat flow equation derived in the '869 application is:

$$q = \Delta p + \Delta T_0 \cdot \left(\frac{R_r - R_s}{R_r \cdot R_s}\right) - \frac{\Delta T}{R_r} + (C_r - C_s) \cdot \frac{dT_s}{d\tau} - C_r \cdot \frac{d\Delta T}{d\tau}$$

The first term is the difference in power supplied to the sample position versus the power supplied to the reference position. The second term accounts for differences between the thermal resistances of the sample and reference holders. The third term accounts for the heat flow that results from the difference in temperature between the sample and reference. The fourth term is the heat flow resulting from imbalances in thermal capacitance between the sample and reference holders. The fifth term reflects heat flow resulting from differences in heating rate between the sample and reference holders.

Heat flow results from that invention show improved dynamic response and hence improved resolution along with improvements in the DSC baseline heat flow. However, the heat flow signal obtained from the practice of that invention still includes the effects of the sample pans.

Modulated Differential Scanning Calorimetry

Modulated Differential Scanning Calorimetry (MDSC) can be used with both heat flux and power compensation DSCs. In MDSC, the temperature program of the DSC cell consists of periodic temperature fluctuations superimposed on a conventional program comprising constant heating rate segments. The measured heat flow is periodic, having the same period as the temperature program while the amplitude and phase angle of the heat flow signal change in response to the sample heat flow. In the preferred embodiment, sample heat flow is comprised of reversing and nonreversing components. The reversing heat flow component is the result of heat storage due to the specific heat capacity of the sample, while the remainder of the total heat flow is the nonreversing heat flow component. Separation of the total heat flow signal into reversing and nonreversing components consists of determining the reversing heat flow, which is subtracted from the total heat flow, leaving the nonreversing heat flow.

The heat capacity of a body is the product of mass and specific heat capacity and is defined by:

$$q = C \cdot \frac{dT}{d\tau},$$

where C is the heat capacity, q is rate of heat flow to or from the body, T is the temperature of the body and τ is time. For MDSC, the applied temperature modulation is generally sinusoidal, so the sample temperature is also sinusoidal:

$$T = \bar{T} \cdot \sin(\omega \cdot \tau - \phi) \quad \omega = \frac{2 \cdot \pi}{P}$$

The bar over the T indicates temperature amplitude; P is the period of the modulation and φ is the phase angle between the applied and the resultant temperature modulations. Differentiate temperature and substitute into the heat capacity equation:

$$q = C \cdot \bar{T} \cdot \omega \cdot \cos(\omega \cdot \tau - \phi)$$

Obviously, the heat flow must also be a cosine for the equality to hold:

$$\bar{q} \cdot \cos(\omega \cdot \tau - \phi) = C \cdot \bar{T} \cdot \omega \cdot \cos(\omega \cdot \tau - \phi)$$

The bar over q indicates heat flow amplitude. Solve for the heat capacity:

$$C = \frac{\overline{q}}{\omega \cdot \overline{T}}$$

This equation is used to find the sample heat capacity, which is used to calculate the reversing heat flow in MDSC. The MDSC deconvolution algorithm as described in U.S. Pat. No. 5,224,775 determines the temperature and heat flow amplitudes. The reversing heat flow is the heat capacity multiplied by the underlying heating rate:

$$q_{rev} = C \cdot \left\langle \frac{dT}{d\tau} \right\rangle$$

The ⟨ ⟩ brackets indicate averaging over an interval comprising an integer multiple of periods, with evaluation at the central point of the interval.

To obtain the correct value of the sample heat capacity from the measurement, a heat capacity calibration factor is applied to the measured heat capacity:

$$C_p = K_c \cdot \frac{\overline{q}}{\omega \cdot \overline{T}}$$

The calibration factor is strongly dependent upon period, as shown in FIG. 1 for isothermal MDSC experiments with 0.05 K and 0.2 K temperature amplitudes, and as explained in A. Boller, Y. Jin, B. Wunderlich "Heat Capacity Measurement by Modulated DSC at Constant Temperature", Journal of Thermal Analysis, Vol. 42 (1994) 307–330. Such large calibration factors suggest that the heat capacity equation used in MDSC is not a good model for sample heat flow. As is known to one of ordinary skill in this field, the heat capacity equation is not limited to sinusoidal oscillations. It may be applied to any periodic oscillation.

Nonreversing heat flow is just the total averaged heat flow minus the reversing component:

$$q_{non} = q_{tot} - q_{rev}$$

It is clear that the key to obtaining accurate separation of the reversing and nonreversing heat flow is accurate calculation of the sample heat capacity.

The heat capacity equation is conventionally used in MDSC to find the reversing heat flow. It is a differential heat flow, i.e., it is the difference in heat flow between the sample and an inert reference:

$$q = q_s - q_r$$

Consider the specific heat capacity equation for two bodies, the sample and its pan and a reference (if used) and its pan:

$$q_s = C_{sm} \cdot \frac{dT_{sm}}{d\tau} \quad q_r = C_{rm} \cdot \frac{dT_{rm}}{d\tau}$$

With a sinusoidal temperature modulation applied, the differential heat flow as measured by DSC is:

$$q = C_{sm} \cdot \overline{T_{sm}} \cdot \cos(\omega \cdot \tau - \phi_{sm}) - C_{rm} \cdot \overline{T_{rm}} \cdot \cos(\omega \cdot \tau - \phi_{rm})$$

This equation cannot be solved for sample heat capacity resulting in a simple equation using the heat flow and temperature amplitudes, because the sample and reference heat flows are not in phase, and because the sample and reference temperature amplitudes differ.

The total sample heat capacity consists of the sample heat capacity plus the pan heat capacity:

$$C_{sm} = C_{ss} + C_{sp}$$

$C_{ss}$ is the sample heat capacity and $C_{sp}$ is the sample pan heat capacity.

Similarly, the total reference heat capacity consists of the reference heat capacity plus the pan heat capacity:

$$C_{rm} = C_{rs} + C_{rp}$$

$C_{rs}$ is the reference heat capacity and $C_{rp}$ is the reference pan heat capacity.

If the period of the modulation is relatively large and the sample mass is small, the phase and amplitude difference between the sample and reference temperatures become small and the differential heat flow equation becomes:

$$q = (C_{sm} - C_{rm}) \cdot \overline{T_{sm}} \cdot \cos(\omega \cdot \tau - \phi_{sm})$$

This equation can be solved to find the difference between sample and reference heat capacity in the same manner as the heat flow equation for a single body. If the reference pan is empty, $C_{rs} = 0$ and:

$$C_{sm} - C_{rm} = C_{ss} + C_{sp} - C_{rp}$$

If the sample and reference pans have the same mass:

$$C_{ss} = C_{sm} - C_{rm}$$

And the measured sample heat capacity is close to the correct value; i.e. the heat flow calibration factor $K_c$ shown in FIG. 1 is very nearly one. This explains why the heat capacity calibration factor is close to one for long modulation periods.

SUMMARY OF THE INVENTION

The present invention can be applied to either heat flux or power compensation DSCs that can independently measure the sample and reference heat flows, and that account for differences in heating rate between the sample and reference pans and the difference in heating rate between the sample and reference (if a reference is used). FIGS. 1 and 2 are schematic diagrams of thermal network models for heat flux DSCs and power compensation DSCs, respectively.

Heat Flux DSCs

As applied to heat flux DSCs, the present invention measures the differential heat flow to the sample based upon a single absolute temperature measurement and two differential temperature measurements. Differential scanning calorimeters of the present invention have substantially improved resolution over conventional instruments, with an empty-cell heat flow that is much closer to zero than that obtained in conventional instruments.

Temperature Measurements

In the present invention, the differential heat flow to the sample with respect to the reference is calculated from measurements of the absolute temperature of the base of the sensor, the differential temperature between the sample position and the base of the sensor, and the differential temperature between the sample and reference positions. The differential temperatures are measured using a sample temperature detector (e.g., a sample area temperature detector), a reference temperature detector (e.g., a reference area temperature detector) and a base temperature detector.

The base temperature detector (which measures the temperature of the base of the sensor near its connection to the oven) is used to control the oven temperature. The sample temperature is measured by measuring the difference between the sample temperature and the base temperature, and subtracting that difference from the base temperature to obtain the sample temperature, i.e., the sample temperature is obtained from $T_s=T_0-\Delta T_0$. By making a single absolute temperature measurement $T_0$, and a differential temperature measurement between the base and sample positions, any relative errors in absolute temperature measurements due to differences in temperature sensors are eliminated. Also, this structure minimizes the drift of sample temperature during isothermal segments. The heat flow signal that results from this structure has improved baseline performance and improved dynamic response. Additionally, because the heat flow signal is greater during a transition, the calorimeter has greater sensitivity.

The sensor constructed according to the present invention exhibits improved independence between the sample and reference positions. For example, whereas in a prior art heat flux instrument, a deviation in the temperature of the sample position of 13.4% was observed when a sample of indium is placed on the reference position and heated through the melt, in an exemplary experiment with the present invention that deviation is only about 1.4%, i.e., the present invention exhibits an improvement by about an order of magnitude over the prior art instruments. Thus sensors constructed according to the present invention are "effectively independent," because they exhibit a temperature deviation at the sample position when an indium sample is placed on the reference position of less than about 1.5% of the temperature deviation at the sample position when an indium sample is placed on the sample position.

Calibration

In a first preferred embodiment of the present invention, the differential scanning calorimeter of the present invention is calibrated by running two separate experiments. These experiments determine the four sensor thermal parameters, $C_s$ (the sensor sample thermal capacitance), $C_r$ (the sensor reference thermal capacitance), $R_s$ (the sensor sample thermal resistance) and $R_r$ (the sensor reference thermal resistance) experimentally, and thus calibrate the heat flow sensor.

The first experiment is performed with an empty DSC cell. The DSC cell is first held at an isothermal temperature that is below the temperature range of the calibration, for a time segment sufficient to ensure complete equilibration of the sensor. The DSC cell is then heated at a constant heating rate to a temperature above the temperature range of the calibration, and then held at that temperature for another isothermal segment, for a time segment sufficient to ensure equilibration of the sensor at that temperature. This first experiment is used to calculate the sample and reference time constants as a function of temperature over the calibrated temperature range.

The heat flow balance equation for the sample side of the sensor is:

$$q_s = \frac{T_0 - T_s}{R_s} - C_s \cdot \frac{dT_s}{d\tau}$$

where $\tau$ represents time, $q_s$ is the heat flow to the sample and the sample pan, $R_s$ is the sensor sample thermal resistance, and $C_s$ is the sensor sample thermal capacitance. Similarly, the heat balance equation on the reference side of the sensor is:

$$q_r = \frac{T_0 - T_r}{R_r} - C_r \cdot \frac{dT_r}{d\tau}$$

where $q_r$ is the heat flow to the reference and the reference pan, $R_r$ is the sensor reference thermal resistance, and $C_r$ is the sensor reference thermal capacitance.

The heat flow to the sample and the heat flow to the reference should be zero (since the DSC cell is empty). Accordingly, if $q_s$ and $q_r$ are set equal to zero in the heat balance equations for the sample and reference sides of the sensor, the time constants for the sample and reference are given by:

$$\tau_s = C_s R_s = \frac{\Delta T_0}{\left(\frac{dT_s}{d\tau}\right)}$$

and $$\tau_r = C_r R_r = \frac{\Delta T_0 + \Delta T}{\frac{dT_s}{d\tau} - \frac{d\Delta T}{d\tau}}$$

respectively, where $\Delta T_0=T_0-T_S$ and $\Delta T=T_s-T_r$. These results are stored as a function of temperature.

The second experiment uses a pair of calibration samples without pans. The calibration samples may have the same mass, or may have different masses. Preferably, the calibration samples are sapphire samples (e.g., monocrystalline sapphire disks), preferably weighing 25 mg or more. Other reference materials with well-known specific heats and no transitions in the temperature range of the calibration may be used instead of sapphire (in which case $C_{sapph}$ would be replaced in the following equations by $C_{mat}$ where $C_{mat}$ is the specific heat of the other reference material).

The sample and reference heat flows from the heat balance equations are set as follows:

$$q_s = m_s \cdot C_{sapph} \cdot \frac{dT_{ss}}{d\tau}$$

$$q_r = m_r \cdot C_{sapph} \cdot \frac{dT_{rs}}{d\tau}$$

where $m_s$, $m_r$ are the masses of the sample and reference sapphires, respectively, $C_{sapph}$ is the specific heat of sapphire and $T_{ss}$ and $T_{rs}$ are the temperatures of the sample and reference sapphire.

Assume:

$$\frac{dT_{ss}}{d\tau} = \frac{dT_s}{d\tau} \text{ and } \frac{dT_{rs}}{d\tau} = \frac{dT_r}{d\tau}$$

Substituting for $q_s$ and $T_{ss}$ in the sample heat balance equation and solving for the sensor sample thermal capacitance $C_s$:

$$C_s = \frac{m_s \cdot Csapph}{\frac{\Delta T_0}{\left(\frac{dT_s}{d\tau}\right) \cdot \tau_s} - 1}$$

Substituting for $q_r$ and $T_{rs}$ in the reference heat balance equation and solving for the sensor reference thermal capacitance $C_r$:

$$C_r = \frac{m_r \cdot C_{sapph}}{\left(\frac{dT_s}{d\tau} - \frac{d\Delta T}{d\tau}\right) \cdot \tau_r} - 1$$

The results from the second experiment using sapphire (or another well-known calibration material) using the time constants for DSC cell obtained in the first experiment are then used to calculate the sample and reference sensor heat capacities as a function of temperature. Finally, the sensor sample and reference thermal resistances are calculated from the time constants and the sensor thermal capacitances:

$$R_s = \frac{\tau_s}{C_s} \text{ and } R_r = \frac{\tau_r}{C_r}$$

A second preferred embodiment is similar to the first embodiment, but uses sapphire (or another material with a well-known heat capacity and no transitions in the temperature range of interest) calibration samples in both the first and the second calibration experiments. The calibration equations and their derivation for this embodiment are described below.

Power Compensation DSCs

As applied to power compensation differential scanning calorimeters, the present invention uses differential temperature measurements, a single temperature measurement, a differential power measurement, and a five term heat flow equation to model the instrument. The present invention is also a method by which the thermal parameters required to apply the five term heat flow equation are determined. Differential scanning calorimeters employing this invention will have empty DSC cell heat flow that is much closer to zero (leading to improved baselines) and will have substantially improved resolution over conventional instruments.

In a preferred embodiment, the two differential temperature measurements are the differential temperature $\Delta T_0$ across thermal resistance $R_s$, and the differential temperature $\Delta T$ between the sample and reference holders. The absolute temperature of the sample holder and the power difference between the sample and reference holders are also measured (i.e., the differential power to the sample with respect to the reference). Additionally, the four thermal parameters, $R_s$, $R_r$, $C_s$ and $C_r$ must be known. The use of two differential temperature measurements allows the use of a heat flow model that includes all five terms of the five term heat flow equation. The heat flow signal that results has improved baseline performance and improved dynamic response. Additionally, because the heat flow signal is greater during a transition, the calorimeter has greater sensitivity.

Other choices of the two differential temperature measurements are also suitable, as explained below.

The present invention also comprises a method by which the four thermal parameters $C_s$, $C_r$, $R_s$, $R_r$ are determined. This determination constitutes heat flow calibration of the DSC.

Heat flow calibration requires two experiments from which the four thermal parameters can be calculated. The first experiment is performed with an empty DSC cell. The DSC program begins with an isothermal temperature segment at a temperature below the lowest temperature of the desired calibration range, followed by a constant heating rate temperature ramp, and ending with an isothermal temperature segment above the highest temperature of the desired calibration range. The heating rate should be the same as the heating rate that is to be used for subsequent experiments. The second calibration experiment is performed with sapphire samples without pans in both the sample and reference holders. The same thermal program is used for the second experiment as was used for the first (empty DSC) experiment. The two calibration experiments and the calculation of the thermal parameters based on the experiments are explained in detail below.

Improved Calculation

The present invention also comprises an improved method for calculating sample heat flow in a differential scanning calorimeter that can be used with both heat flux and power compensation DSCs.

Differential scanning calorimeters employing the improved calculation of the present invention furnish a sample heat flow signal that is a substantially more accurate representation of the sample heat flow during the entire DSC experiment, essentially free of the smearing effects that are present in conventional DSC. Accordingly, DSCs using the present invention will have greatly improved resolution. For example, kinetic analysis requiring partial integration of peak areas can be practiced using the present invention whereas partial integration is of limited use with conventional DSCs, due to the distortions of the sample heat flow signal.

The result is a more accurate measurement of the sample heat flow during transitions in which the heating rate of the sample differs from that of the reference. Resolution is improved because the return to baseline of the heat flow signal at the completion of a transformation is much more rapid.

Modulated DSCs

The '949 application discloses a DSC in which the sample and reference heat flows may be measured separately. The equations for heat flow to the sample and its pan and to the reference (if used) and its pan are:

$$q_s = \frac{\Delta T_0}{R_s} - C_s \cdot \frac{dT_s}{d\tau} \qquad q_r = \frac{\Delta T_0 + \Delta T}{R_r} - C_r \cdot \left(\frac{dT_s}{d\tau} - \frac{d\Delta T}{d\tau}\right)$$

Two temperature differences are used, the conventional $\Delta T$ between sample and reference positions of the sensor and an additional signal $\Delta T_0$ between the sample position and the base of the sensor. Thermal resistances and capacitances, Rs, Rr, Cs and Cr of the sensor are determined form the calibration methods disclosed in that invention. Having the individual heat flow signals allows the sample and reference heat capacities to be measured using the heat capacity equation:

$$C_{sm} = \frac{q_s}{\omega \cdot T_{sm}} \qquad C_{rm} = \frac{q_r}{\omega \cdot T_{sm}}$$

The temperature and heat flow amplitudes are found using the deconvolution algorithm described in U.S. Pat. No. 5,224,775, which is incorporated by reference herein. Measured temperatures in the DSC cell are the temperatures of the sample and reference platforms, not $T_{sm}$ and $T_{rm}$ as required by the sample and heat capacity equations. However, $T_{sm}$ and $T_{rm}$ can be found using the equations for heat flow between the pans and the sensor:

$$q_s = \frac{T_s - T_{sm}}{R_{sm}} \qquad q_r = \frac{T_r - T_{rm}}{R_{rm}}$$

Solving for $T_{sm}$ and $T_{rm}$:

$$T_{sm} = T_s - q_s \cdot R_{sm} \qquad T_{rm} = T_r - q_r \cdot R_{rm}$$

Temperatures $T_s$ and $T_r$ are measured, heat flows $q_s$ and $q_r$ are measured, and predetermined values for $R_{sm}$ and $R_{rm}$ are used. Temperature $T_r$ is not measured directly, but is obtained by combining $T_s$ and $\Delta T$, so that the equation for $T_{rm}$ becomes:

$$T_{rm} = T_s - \Delta T - q_r \cdot R_{rm}$$

It is implied that the temperatures of the sample and its pan are the same and that the temperature of the reference (if used) and its pan are the same. The pan heat capacities are the product of pan masses and the pan material specific heat capacity:

$$C_{sp} = m_{sp} \cdot c_{pm} \quad C_{rp} = m_{rp} \cdot c_{pm}$$

Substitute the sample pan heat capacity into the equation for measured sample heat capacity and solve for the sample heat capacity:

$$C_{ss} = C_{sm} - m_{ps} \cdot c_{pm}$$

Substitute the reference pan heat capacity into the equation for measured reference heat capacity and solve for pan heat capacity:

$$c_{pm} = \frac{C_{rm} - C_{rs}}{m_{pr}}$$

Substitute into the equation for the sample heat capacity:

$$C_{ss} = C_{sm} - \frac{m_{ps}}{m_{pr}} \cdot (C_{rm} - C_{rs})$$

Finally, substitute the equations for $C_{sm}$ and $C_{rm}$:

$$C_{ss} = \frac{\overline{q_s}}{\omega \cdot \overline{T_{sm}}} - \frac{m_{ps}}{m_{pr}} \cdot \left( \frac{\overline{q_r}}{\omega \cdot \overline{T_{rm}}} - C_{rs} \right)$$

All quantities on the right hand side are measured as described above, except for the heat capacity of the reference material, which must be known. Most DSC experiments are performed with an empty reference pan. In that case the sample heat capacity equation simplifies to:

$$C_{ss} = \frac{\overline{q_s}}{\omega \cdot \overline{T_{sm}}} - \frac{m_{ps}}{m_{pr}} \cdot \frac{\overline{q_r}}{\omega \cdot \overline{T_{rm}}}$$

BRIEF DESCRIPTION OF THE FIGURES

FIG. 1b is a cross sectional view of an embodiment of the sensor shown in FIG. 1a.

DETAILED DESCRIPTION OF THE INVENTION

Heat Flux DSCs

Temperature Measurements

Figure 1:
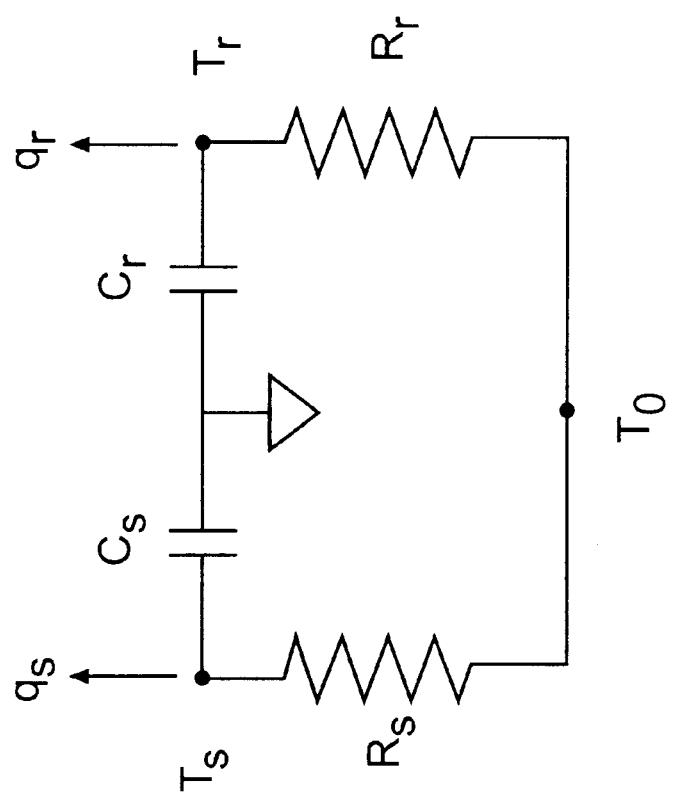
FIG. 1 is a thermal network model of a heat flux differential scanning calorimeter.
Figure 1A:
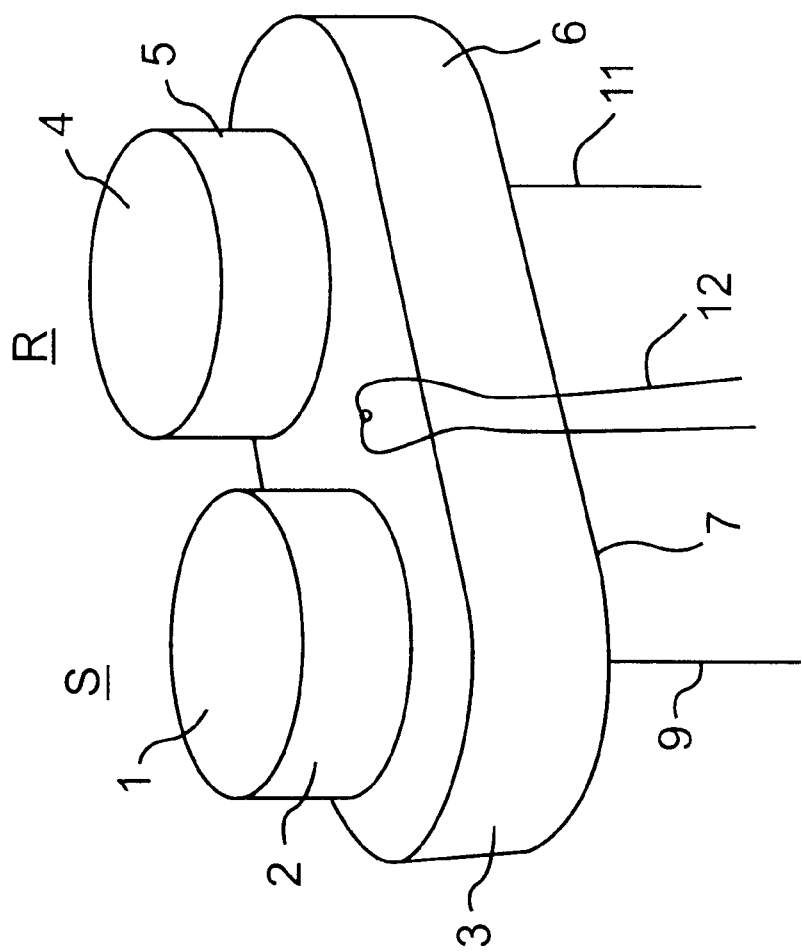
FIG. 1a is a schematic diagram of a heat flux DSC sensor of an embodiment of the present invention.

FIG. 1a is a schematic diagram of an overall view of a preferred embodiment of a heat flux DSC sensor according to the present invention. The sample is loaded in a pan and placed on the sample platform 1. Sample platform 1 is a thin flat circular disk that is attached to the thin wall cylindrical tube 2, which is also joined to the base 3. The reference is loaded in a pan placed on the reference platform 4. Reference platform 4 is a thin flat circular disk that is attached to thin wall cylindrical tube 5, which is also joined to the base 3. The platforms, tubes and base (items 1 through 5) are integral parts of the sensor body 6 which is made of constantan, the negative element of a type E thermocouple. The thin wall tube portions 2 and 5 of the sensor body are the principal contributors to the thermal resistances $R_s$ and $R_r$ of the DSC sensor. The underside of the base 7 is a flat surface. This surface is the mounting surface of the sensor used to install the sensor in the DSC oven.

A typical sample thin wall cylindrical tube 2 and reference thin wall cylindrical tube 5 have a height of 0.09 inches, a diameter of 0.187 inches, and a wall thickness of 0.005 inches. The sample platform thickness is also 0.005 inches. Thus the cross sectional area of the tube itself (i.e., the tube's circumference times its thickness) is about 0.00284 square inches, such that the aspect ratio (the ratio of the height of the cylinder to its cross-sectional area) is about 31.5 inches⁻1. The aspect ratio should preferably range from 25 to 35, in order to obtain both good resolution and good sensitivity. The sensor's sensitivity may be increased (at a cost to its resolution), by increasing the height of the cylinder, to, for example, 0.3–0.5 inches. Alternatively, the sensor's resolution may be increased (at a cost to its sensitivity), by reducing the cylinder height to, for example, 0.02 to 0.04 inches.

Figure 1B:
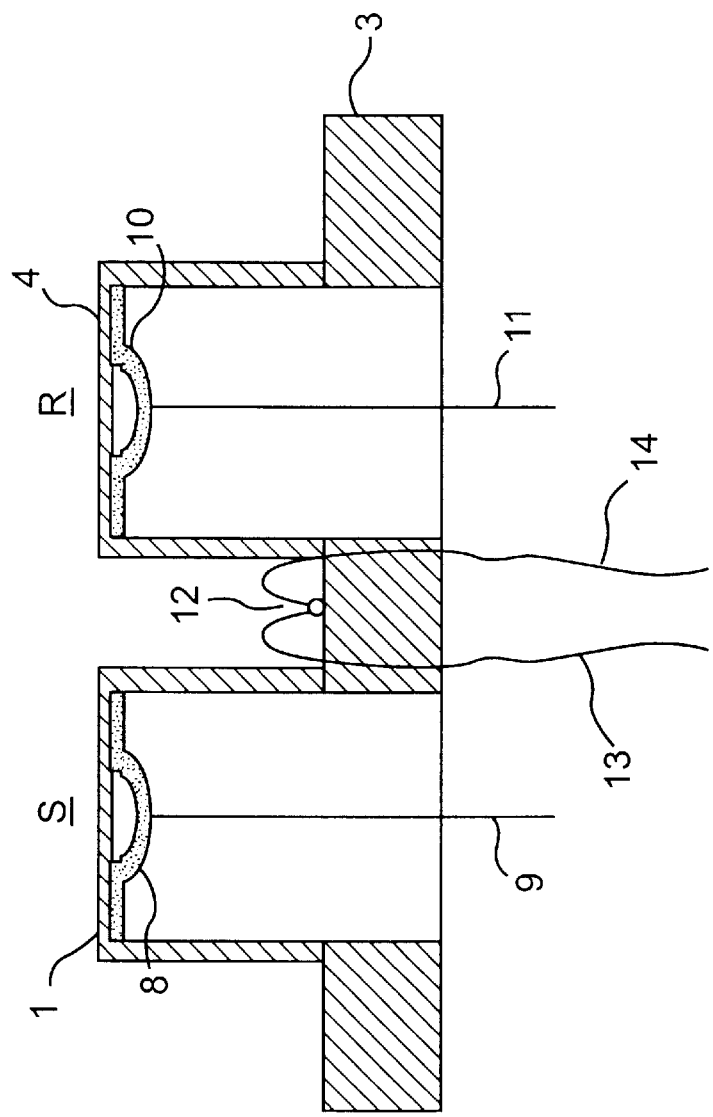

FIG. 1b is a schematic diagram of a cross sectional view through the DSC sensor, taken at a plane perpendicular to and passing through the centers of the sample and reference platforms. A sample area temperature detector 8 is welded concentrically to the underside of the sample platform 1. The area temperature detector is a thin circular disk of chromel that is the thermoelectrically positive element of a type E thermocouple. At the center is a depressed portion to which a chromel wire 9 is welded. The sample area temperature detector 8 is welded to the underside of the sample platform 1 at sixteen places equally spaced in a circular pattern concentric to the sample area detector 8 and sample platform 1, thus forming sixteen thermoelectric junctions in parallel between the constantan sample platform 1 and the sample area temperature detector 8.

A reference area temperature detector 10 is welded concentrically to the underside of the reference platform 4. The reference area temperature detector 10 is a thin circular disk of chromel that is the thermoelectrically positive element of a type E thermocouple. At the center is a depressed portion to which a chromel wire 11 is welded. The reference area temperature detector 10 is welded to the underside of the reference platform 4 at sixteen places equally spaced in a circular pattern concentric to the reference area temperature detector 10 and reference platform 4, thus forming sixteen thermoelectric junctions in parallel between the constantan reference platform 4 and the reference area temperature detector 10. A type E thermocouple 12 is welded to the center of the top surface of the base 3. Lead wire 13 is the chromel and lead wire 14 is the constantan element of the type E thermocouple.

Figure 1C:
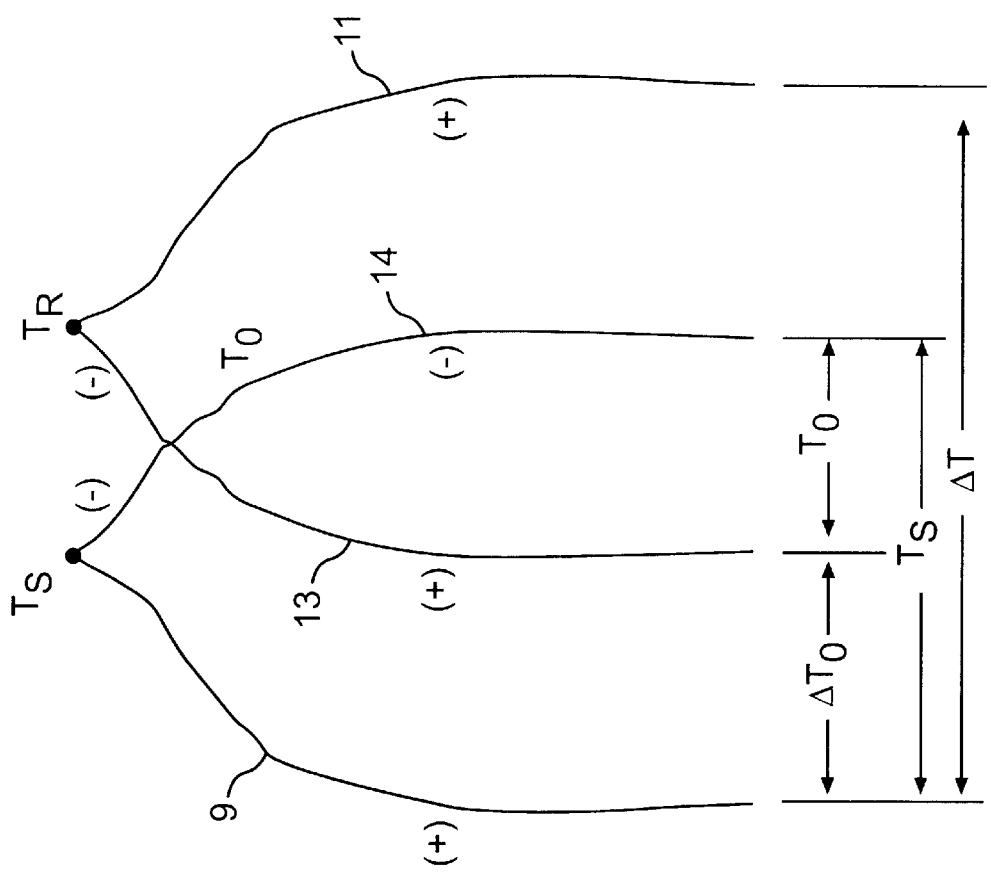
FIG. 1c is an electrical schematic showing how the thermocouples shown in FIGS. 1a and 1b are used to measure the absolute and differential temperatures in the present invention.

FIG. 1c is a schematic representation of the thermocouple configuration, showing how the voltages representing $\Delta T_0$, $T_s$ and $\Delta T$ are measured. The (+) signs indicate the chromel leads and the area detectors. The (−) signs indicate the constantan sensor body and the constantan lead. As shown in FIG. 1c, the voltage representing the differential temperature $\Delta T$ between the sample and the reference is measured between chromel lead wire 9 and chromel lead wire 11. The voltage representing the differential temperature $\Delta T_0$ between the sample and the base is measured between chromel lead wires 9 and 13. The sixteen parallel thermocouple junctions between area detectors 8 and 10 and sample and reference platforms 1 and 4, respectively, allow the measurement of the difference between the average temperatures of the sample and reference platforms as described in U.S. Pat. No. 4,095,453, which is incorporated by reference herein. Area detector 8 also allows measurement of the difference between the average temperature of the sample platform and the temperature at the base of the sensor. The area detectors and associated parallel thermocouples reduce the sensitivity of the $\Delta T$ and $\Delta T_0$ measurements to any variations in the position of the pans upon the sensor, as well as the sensitivity due to variations in the contact resistance between the pan and the sensor. Type E thermocouple 12 is used to measure $T_0$, the temperature at the base of the sensor. As shown in FIG. 1c, the voltage representing this temperature appears between lead wires 13 and 14. The sample temperature representing $T_s$ is obtained by combining voltages representing $T_0$ and $\Delta T_0$ to obtain the voltage representing $T_s$ that would appear between lead wires 9 and 14. While the preferred embodiment discloses a structure using combinations of the thermoelectric materials constantan and chromel, one of ordinary skill in the art would recognize that other thermocouple materials could be used to make the same measurements and achieve the same results.

Those skilled in the art would also recognize that there are numerous other configurations whereby a single temperature measurement and two differential measurements could be used with a slightly different four-term heat flow equation to obtain the same result. There are three possible choices for the temperature measurement: the sample platform temperature $T_s$, the reference platform temperature $T_r$ and the sensor base temperature $T_0$. Each of these can be used with any two of the three differential temperature measurements to achieve the same result. Thus, in the preferred embodiment described above, the base temperature $T_0$ is used for the absolute temperature measurement, with differential temperature measurements $T_0-T_s$ and $T_s-T_r$. The base temperature $T_0$ could also be used with differential measurements $T_0-T_s$ and $T_0-T_r$ or with $T_s-T_r$ and $T_0-T_r$. The reference temperature $T_r$ can be used as the absolute temperature measurement with differential temperature measurements $T_s-T_r$ and $T_0-T_r$ or with $T_0-T_r$ and $T_0-T_s$ or with $T_s-T_r$ and $T_0-T_s$. The sample temperature $T_s$ can be used as the absolute temperature measurement with $T_0-T_s$ and $T_s-T_r$, or with $T_0-T_s$ and $T_0-T_r$ or with $T_0-T_r$ and $T_s-T_r$. Thus, there are eight additional configurations that could give the same information if the four-term heat flow equation is rewritten accordingly. All nine of the possible configurations are within the scope of the present invention.

First Preferred Method for Determining Sensor Thermal Parameters

Preferably, the sensor is calibrated prior to use. The sensor is calibrated by determining the values of sensor thermal parameters $C_s$, $C_r$, $R_s$, and $R_r$.

As described above, in a first preferred embodiment of the present invention, the sensor is calibrated by, performing two sequential measurements, the first with an empty DSC cell, and the second with a sapphire sample in the sample position and another sapphire sample in the reference position. Preferably, the sapphire samples should each weigh at least 25 mg.

As described above, for the first calibration experiment a thermal program starting with an isothermal temperature segment at a temperature below the calibration range, followed by a constant heating rate temperature ramp, and ending with an isothermal segment above the calibration range is applied to the empty DSC cell. Preferably, the heating rate used during calibration should be the same as that used for subsequent experiments. Preferably, the temperature range of the calibration equals or exceeds the temperature range of the subsequent experiments.

The sample time constant as a function of temperature is then given by:

$$\tau_s = C_s R_s = \frac{\Delta T_0}{\left(\frac{dT_s}{d\tau}\right)}$$

and the reference time constant is given by:

$$\tau_r = C_r R_r = \frac{\Delta T_0 + \Delta T}{\frac{dT_s}{d\tau} - \frac{d\Delta T}{d\tau}}$$

The results from the empty DSC experiment are used to calculate and store the time constants as a function of sample temperature.

As described above, for the second calibration experiment, a pair of sapphire calibration samples is placed on the sample and reference positions of the sensor. The thermal program that was used for the empty DSC experiment is then applied to the DSC cell.

As shown above, the sensor sample thermal capacitance is given by:

$$C_s = \frac{m_s \cdot C_{sapph}}{\frac{\Delta T_0}{\left(\frac{dT_s}{d\tau}\right) \cdot \tau_s} - 1}$$

and the sensor reference thermal capacitance is given by:

$$C_r = \frac{m_r \cdot C_{sapph}}{\frac{\Delta T_0 + \Delta T}{\left(\frac{dT_s}{d\tau} - \frac{d\Delta T}{d\tau}\right) \cdot \tau_r} - 1}$$

These equations are used with the time constants from the empty DSC cell experiments to calculate the sample and reference sensor heat capacities as a function of temperature. Finally, the sensor thermal resistances are computed from the time constants and sensor thermal capacitances:

$$R_s = \frac{\tau_s}{C_s} \text{ and } R_r = \frac{\tau_r}{C_r}$$

The thermal capacitances and resistances are used in the DSC heat flow calculation either as tabular data that are interpolated between points or the data may be fitted with a polynomial. Generally, the thermal capacitance and resistance data are smooth and well behaved so that a low order polynomial fit gives sufficient precision.

Second Preferred Method for Determining Sensor Parameters

A second preferred method for calibrating the DSC sensor is to perform two sequential DSC scans with samples in both scans, using, e.g., sapphire samples. The sample masses on both sample and reference sides must be different for the two scans.

As for the first embodiment, we assume the heating rates of the samples are the same as the heating rates of the sample and reference sides of the sensor.

For the sample side, the heat flows are given by:

$$q_{s1} = m_{s1} \cdot C_{sapph} \cdot \frac{dT_{s1}}{d\tau}$$

$$q_{s2} = m_{s2} \cdot C_{sapph} \cdot \frac{dT_{s2}}{d\tau}$$

The numeric subscripts indicate scans 1 and 2.

The heat balance equation for the sample side for scans 1 and 2 are then:

$$q_{s1} = \frac{\Delta T_{01}}{R_s} - C_s \cdot \frac{dT_{s1}}{d\tau}$$

$$q_{s2} = \frac{\Delta T_{02}}{R_s} - C_s \cdot \frac{dT_{s2}}{d\tau}$$

Solving the heat balance equations simultaneously gives, $$C_s = \frac{\Delta T_{01} \cdot q_{s2} - \Delta T_{02} \cdot q_{s1}}{\Delta T_{02} \frac{dT_{s1}}{d\tau} - \Delta T_{01} \frac{dT_{s2}}{d\tau}}$$

$$R_s = \frac{\Delta T_{02} \cdot \frac{dT_{s1}}{d\tau} - \Delta T_{01} \cdot \frac{dT_{s2}}{d\tau}}{q_{s2} \cdot \frac{dT_{s1}}{d\tau} - q_{s1} \cdot \frac{dT_{s2}}{d\tau}}$$

For the reference side:

$$q_{r1} = m_{r1} \cdot C_{sapph} \cdot \frac{dT_{r1}}{d\tau}$$

$$q_{r2} = m_{r2} \cdot C_{sapph} \cdot \frac{dT_{r2}}{d\tau}$$

The heat balance equations for the reference side for samples 1 and 2 are:

$$q_{r1} = \frac{T_{01} - T_{r1}}{R_r} - C_r \cdot \frac{dT_{r1}}{d\tau}$$

$$q_{r2} = \frac{T_{02} - T_{r2}}{R_r} - C_r \cdot \frac{dT_{r2}}{d\tau}$$

Substituting as above:

$$q_{r1} = \frac{\Delta T_{01} + \Delta T_1}{R_r} - C_r \cdot \left(\frac{dT_{s1}}{d\tau} - \frac{d\Delta T_1}{d\tau}\right)$$

$$q_{r2} = \frac{\Delta T_{02} + \Delta T_2}{R_r} - C_r \cdot \left(\frac{dT_{s2}}{d\tau} - \frac{d\Delta T_2}{d\tau}\right)$$

Solving simultaneously gives:

$$R_r = \frac{(\Delta T_{02} + \Delta T_2) \cdot \left(\frac{dT_{s1}}{d\tau} - \frac{d\Delta T_1}{d\tau}\right) - (\Delta T_{01} + \Delta T_1) \cdot \left(\frac{dT_{s2}}{d\tau} - \frac{d\Delta T_2}{d\tau}\right)}{q_{r2} \cdot \left(\frac{dT_{s1}}{d\tau} - \frac{d\Delta T_1}{d\tau}\right) - q_{r1} \cdot \left(\frac{dT_{s2}}{d\tau} - \frac{d\Delta T_2}{d\tau}\right)}$$

$$C_r = \frac{(\Delta T_{01} + \Delta T_1) \cdot q_{r2} - (\Delta T_{02} + \Delta T_2) \cdot q_{r1}}{(\Delta T_{02} + \Delta T_2) \cdot \left(\frac{dT_{s1}}{d\tau} - \frac{d\Delta T_1}{d\tau}\right) - (\Delta T_{01} + \Delta T_1) \cdot \left(\frac{dT_{s2}}{d\tau} - \frac{d\Delta T_2}{d\tau}\right)}$$

Thus, using the results from two DSC scans with samples with different masses on both the sample and reference sides, the sensor thermal parameters can be computed. Note that one of the two calibration experiments may be performed with an empty DSC, in which case $m_s$ and $m_r$ are zero, and $q_s$ and $q_r$ are also zero (this actually reduces to the first preferred calibration method, i.e., the first method is just a special case of the second method with $m_{s1}=m_{r1}=0$).

The DSC Enclosure

The DSC sensor measures the differential heat that flows through the DSC sensor between the sample platform and the DSC enclosure, with respect to the heat that flows through the DSC sensor between the reference platform and the DSC enclosure. However, a small amount of heat flows directly between the sample and reference platforms and the DSC enclosure by heat conduction through the gas, by radiation exchange, and by convection.

Such extraneous heat flows between the sample and reference platforms and the enclosure are not measured and hence, especially to the extent that the extraneous heat flows from the sample platform are not balanced by the extraneous heat flows from the reference platform, contribute to errors in the differential heat flow measurement. The magnitude of this error depends upon the variation of temperature within the DSC enclosure. Increased uniformity of temperature within the enclosure reduces the overall extraneous heat flow generally, and also reduces the difference between the extraneous heat flow from the sample platform and the extraneous heat flow from the reference platform.

In particular, the lid of the DSC enclosure is an important contributor to non-uniformity within the enclosure, because it exchanges heat with the insulation surrounding the enclosure (which in turn exchanges heat with the DSC cell surroundings) and because it has relatively poor thermal contact with the body of the enclosure (because it must be easily removed). Thus, the temperature of the lid may be substantially different from the temperature of the body of the enclosure, and this non-uniformity is responsible for the greatest portion of the extraneous heat flow.

Figure 1D:
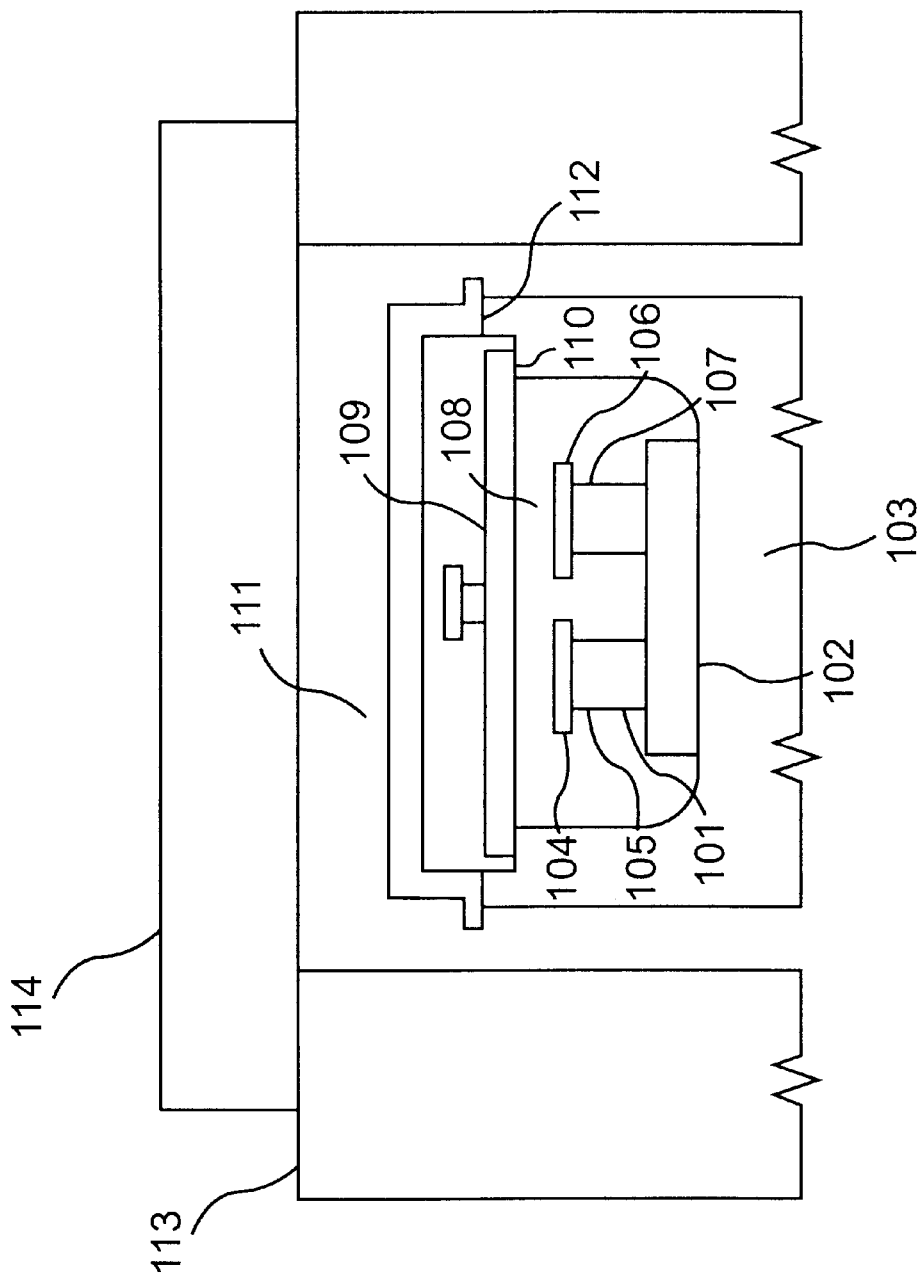
FIG. 1d is a schematic diagram of a cross-section of the DSC cell assembly for a preferred embodiment of the present invention.

In a preferred embodiment of the present invention, shown in FIG. 1d, non-uniformity within the DSC enclosure is greatly reduced by adding a second outer lid that encloses the first inner lid and contacts the body of the DSC enclosure. In this embodiment, heat is exchanged between the insulation surrounding the enclosure and the outer lid. This essentially eliminates heat flow through the DSC enclosure lid, greatly reducing the temperature difference between the body and the lid of the DSC enclosure and substantially reducing the extraneous heat flow.

FIG. 1d is a schematic diagram of a cross section through the upper portion of the DSC cell assembly (the lower portion is omitted for clarity). The DSC sensor of the present invention 101 is mounted to the lower surface 102 of the body 103 of the DSC enclosure. Typically, the sensor is brazed to the enclosure to ensure that heat flows easily and uniformly between the sensor and the enclosure. The sample in a pan 104 is placed on the sensor sample position 105, a reference (if used) in a pan 106 is placed on the sensor reference position 107. Because the sample and reference pans are in direct contact with the DSC sensor, heat flows well between them and the sensor, guaranteeing that very nearly all heat flow to and from the sample and reference is through the sensor, and is therefore measured. The cavity 108 of the DSC enclosure is closed by inner lid 109. Cavity 108 is continuously purged with a purge gas, typically nitrogen (although other gases such as helium or argon may be used).

Because the body of the cavity is fabricated from a single piece of a very high thermal conductivity material (typically silver), its temperature is very uniform. Because inner lid 109 merely rests on surface 110 of enclosure body 103, heat exchange between inner lid 109 and enclosure body 103 is relatively poor. Outer lid 111 completely covers the inner lid 109 and also rests on enclosure body 103 on surface 112, such that inner lid 109 and outer lid 111 do not contact one another. Surrounding the entire upper portion of the DSC enclosure is a thermal insulation enclosure comprising body 113 and removable lid 114 that allows the inner and outer lids of the DSC enclosure to be removed for sample and reference loading and unloading.

Thus adding an outer lid to the DSC enclosure improves temperature uniformity within the DSC enclosure, and substantially reduces errors due to extraneous heat flow.

Improved Calculation

A heat flux DSC sensor according to the invention described above and in the '949 application comprises independent sample and reference measuring sections that may be modeled using a thermal resistance and a thermal capacitance for each of the sample and reference sections as shown in FIG. 1. Thermal resistance and capacitance elements are idealizations of the sensor, which allow simple mathematical expressions describing the thermal behavior of the sensor to be written. $R_s$ and $R_r$ are thermal resistances, $C_s$ and $C_r$ are thermal capacitances representing the sample and reference sections of the sensor. $T_0$, $T_s$ and $T_r$ are the temperatures of the sensor base, sample position and reference positions. The heat flow to the sample and its pan and to the reference and its pan are $q_s$ and $q_r$, respectively.

Performing a heat balance on the sample and reference gives the heat balance equations:

$$q_s = \frac{T_0 - T_s}{R_s} - C_s \cdot \frac{dT_s}{d\tau}$$

$$q_r = \frac{T_0 - T_r}{R_r} - C_r \cdot \frac{dT_r}{d\tau}$$

In the preferred embodiment of the invention described above and in the '949 application, the sensor base temperature $T_0$, the difference between the sensor base and sample position temperatures and the difference between the sample and reference position temperatures are measured. The differential temperatures are defined by:

$$\Delta T = T_s - T_r, \quad \Delta T_0 = T_0 - T_s$$

Substituting into the heat balance equations gives, $$q_s = \frac{\Delta T_0}{R_s} - C_s \cdot \frac{dT_s}{d\tau} \text{ and}$$

$$q_r = \frac{\Delta T_0 + \Delta T}{R_r} - C_r \cdot \left( \frac{dT_s}{d\tau} - \frac{d\Delta T}{d\tau} \right)$$

Sample temperature is obtained from the definition of $\Delta T_0$, $$T_s = T_0 - \Delta T_0$$

Thermal resistances and capacitances of the sensor as a function of temperature are obtained using the calibration method described above and in the '949 application. Using thermal resistances and capacitances obtained by calibration with the temperatures and differential temperatures measured during a DSC experiment allows the sample and reference heat flows, $q_s$ and $q_r$ to be found. As used in the invention disclosed in the '949 application and in conventional DSC, the difference between sample and reference heat flows is the desired result.

$$q = q_s - q_r$$

As noted above, the sample and reference heat flows include the heat flow to the sample and reference and to their pans.

$$q_s = q_{ss} + q_{ps}, \quad q_r = q_{rs} + q_{pr}$$

Where $q_{ss}$ is the sample heat flow, $q_{ps}$ is the sample pan heat flow, $q_{rs}$ is the reference heat flow and $q_{pr}$ is the reference pan heat flow. Because the pans and the reference do not have transitions, their heat flows are just the sensible heat associated with their specific heats:

$$q_{ps} = m_{ps} \cdot c_p \cdot \frac{dT_{ps}}{d\tau}$$

$$q_r = m_{pr} \cdot c_p \cdot \frac{dT_{pr}}{d\tau} + m_{rs} \cdot c_{rs} \cdot \frac{dT_{pr}}{d\tau}$$

Where $m_{ps}$ and $m_{pr}$ are the masses of the sample and reference pans, $c_p$ is the specific heat of the pan material, $m_{rs}$ is the mass of the reference material, $c_{rs}$ is the specific heat of the reference material. The sample pan temperature is $T_{ps}$ and the reference pan temperature is $T_{pr}$. It is assumed that the reference material has no transitions, and that it heats at the same rate as the reference pan.

Substituting for the sample pan heat flow and solving for the sample heat flow:

$$q_{ss} = q_s - m_{ps} \cdot c_p \cdot \frac{dT_{ps}}{d\tau}$$

Solving the reference heat flow equation for the pan specific heat and substituting the specific heat into the sample heat flow equation:

$$q_{ss} = q_s - q_r \cdot \frac{m_{ps}}{m_{pr}} \cdot \frac{\frac{dT_{ps}}{d\tau}}{\frac{dT_{pr}}{d\tau}} + \frac{m_{ps}}{m_{pr}} \cdot m_{rs} \cdot c_{rs} \cdot \frac{dT_{ps}}{d\tau}$$

This equation gives the actual sample heat flow, accounting for the sample and reference pan heat flows and the heat flow to the reference. The second term on the right hand side is seen to be the reference heat flow multiplied by the ratio of the sample and reference pan masses and by the ratio of the sample and reference pan heating rates. It accounts for the fact that during a transition, the sample pan heats at a different rate than the reference pan because of the transition heat flow. The third term accounts for the heat flow to the reference material. In most cases, the reference pan is empty and the sample heat flow equation becomes.

$$q_{ss} = q_s - q_r \cdot \frac{m_{ps} \cdot \frac{dT_{ps}}{d\tau}}{m_{pr} \cdot \frac{dT_{pr}}{d\tau}}$$

Both of these equations can be written using different nomenclature, or using different units, or using different, but thermodynamically equivalent algebraic expressions. For example, the two equations can be re-written in heat capacity units by dividing by the heating rate as follows:

$$q'_{ss} = \left( q_s - q_r \cdot \frac{m_{ps} \cdot \frac{dT_{ps}}{d\tau}}{m_{pr} \cdot \frac{dT_{pr}}{d\tau}} + \frac{m_{ps}}{m_{pr}} \cdot m_{rs} \cdot c_{rs} \cdot \frac{dT_{ps}}{d\tau} \right) \cdot \frac{1}{\frac{dT_s}{d\tau}}$$

$$q'_{ss} = \left( q_s - q_r \cdot \frac{m_{ps} \cdot \frac{dT_{ps}}{d\tau}}{m_{pr} \cdot \frac{dT_{pr}}{d\tau}} \right) \cdot \frac{1}{\frac{dT_s}{d\tau}}$$

When the sample heating rate is different from the reference heating rate, the fraction of reference heat flow subtracted from the sample heat flow is greater or less, depending upon whether the sample pan heating rate is greater or less than that of the reference pan. Because the reference heat flow is just the reference pan heat flow, this equation accounts for differences between sample and reference pan heating rates. For example, during a melt in a DSC, the sample pan heating rate falls below the programmed rate, while the reference pan continues to heat at the programmed rate. In a conventional DSC the reference heat flow being subtracted from the sample heat flow is for a pan heating at the programmed rate. Thus, during the melt, too much heat is being subtracted from the sample heat flow and the heat flow signal is too small. During the baseline return, the sample pan is heating faster than the reference pan and insufficient heat flow is subtracted from the sample heat flow. As a consequence, the heat flow signal is too large.

To use the true sample heat flow equation requires that the sample and reference pan temperatures be known so that their derivatives may be taken. Unfortunately, there is no way to measure the pan temperatures directly. However, the pan temperatures can be calculated from the temperature and heat flow signals as follows.

The equations for heat flow from the sensor to the sample and reference pans are:

$$q_s = \frac{T_s - T_{ps}}{R_{ps}}$$

$$q_r = \frac{T_r - T_{pr}}{R_{pr}}$$

Solving for the pan temperatures.

$$T_{ps} = T_s - q_s \cdot R_{ps} \quad T_{pr} = T_r - q_r \cdot R_{pr}$$

Using these equations, pan temperatures and sample heat flows can be calculated from the measured signals.

The pan thermal resistances $R_{ps}$, and $R_{pr}$ depend on the pan configuration, the purge gas used in the DSC and the temperature of the DSC. Several techniques for determining $R_{ps}$ and $R_{pr}$ have been developed in the past and are well-known to one of ordinary skill in the art. For example, one well-known technique is to measure the slope of the onset of a metal melt.

A preferred semi-empirical method for determining $R_{ps}$ and $R_{pr}$ is to use a model equation that models heat exchange between the sample and reference pans and the DSC sensor. Because when two nominally flat surfaces are brought into contact, they only make contact over a small fraction of the projected area of contact (because the surfaces are not perfectly flat), heat exchange could occur in principle through three mechanisms: by direct solid heat conduction through the asperities of the two surfaces in contact, by convection or conduction through the interstitial gas between the surfaces and by radiation between the two surfaces. However, except in cases of an extremely high heat flux and a large temperature difference between the two surfaces, radiation is insignificant. Also, the dominant heat exchange through the gas is by conduction. In that case, the contact thermal resistance between the surfaces can be modeled by heat conduction through two series connected solid conductors (representing each of the surfaces) in parallel with heat conduction through the gas. Using these assumptions to model the DSC pan/sensor heat exchange, the model equation for the DSC pan contact resistance is:

$$R(T) = \frac{1}{\frac{\alpha_P \cdot k_p(T) \cdot \alpha_S \cdot k_S(T)}{\alpha_P \cdot k_P(T) + \alpha_S \cdot k_S(T)} + \alpha_G \cdot k_G(T)}$$

Where, R(T) is the contact resistance as a function of temperature; $k_p(T)$, $k_s(T)$, $k_g(T)$ are thermal conductivities of the pan, sensor and gas; $\alpha_p$, $\alpha_s$ and $\alpha_g$ are geometric factors for the pan, sensor and gas. The geometric factors have the dimension of length—they may be thought of as the ratio of the area normal to the heat flow to the length of the heat conduction path. Thermal conductivities of the sensor, pan and gas are known.

The geometric factors are determined empirically as follows. The contact resistance between the pan and the sample may be measured using MDSC with average heating rate equal to zero. A sample of known heat capacity is loaded into a pan and placed on the sample position of the DSC, and the temperature is modulated sinusoidally at fixed amplitude about a given temperature. Assuming the sample and pan temperatures are the same, a two-temperature model of the DSC may be solved to find the time constant of the pan and sample.

$$\tau_s = \frac{-b_s \pm \sqrt{b_s^2 - 4b_s c_s}}{2a_s}$$

where:

$$a_s = \overline{T}_s^2 \cdot (\omega^4 \cdot (C_s R_s)^2 + \omega^2) - \omega^2 \cdot \overline{T}_0^2$$

$$b_s = 2\overline{T}_s^2 \cdot \omega^2 \cdot C_{ss} \cdot R_s$$

$$c_s = \overline{T}_s^2 \cdot [1 + \omega^2 \cdot ((C_s R_s)^2 + (C_{ss} R_s)^2 + 2 C_s C_{ss} R_s^2)] - \overline{T}_0^2$$

$$R_{ps} = \frac{\tau_s}{C_{ss}}$$

where temperature with an over bar means the modulated temperature amplitude, obtained by the MDSC temperature deconvolution algorithm (as described in U.S. Pat. No. 5,224,775, which is incorporated by reference herein), $C_{ss}$ is the combined heat capacity of the sample and the pan and $\omega$ is the circular frequency of the modulation. The assumption that sample and pan temperatures are the same is justified when the modulation period is sufficiently long (typically 60 seconds or above). A similar set of equations can be written for the reference side of the DSC, and the two contact resistances may be determined in a single experiment.

Using this method for determining the contact resistance at a variety of discrete temperatures, the model equation above may be fitted to the data to determine the geometric parameters $\alpha_p$, $\alpha_s$ and $\alpha_g$. Using a multiplicity of different samples and pans, the experiments may be repeated many times and a statistically determined average value of the contact resistance can be computed.

It must be noted that the method of the present invention cannot be applied to heat flux DSCs generally: it can only be applied to DSCs that separately measure the sample and the reference heat flows. The physical configuration of the apparatus disclosed herein allows the sample and reference heat flows to be measured separately, and this characteristic (although not necessarily the exact embodiment disclosed herein) is required to apply the present invention.

Power Compensation DSCs

Figure 2:
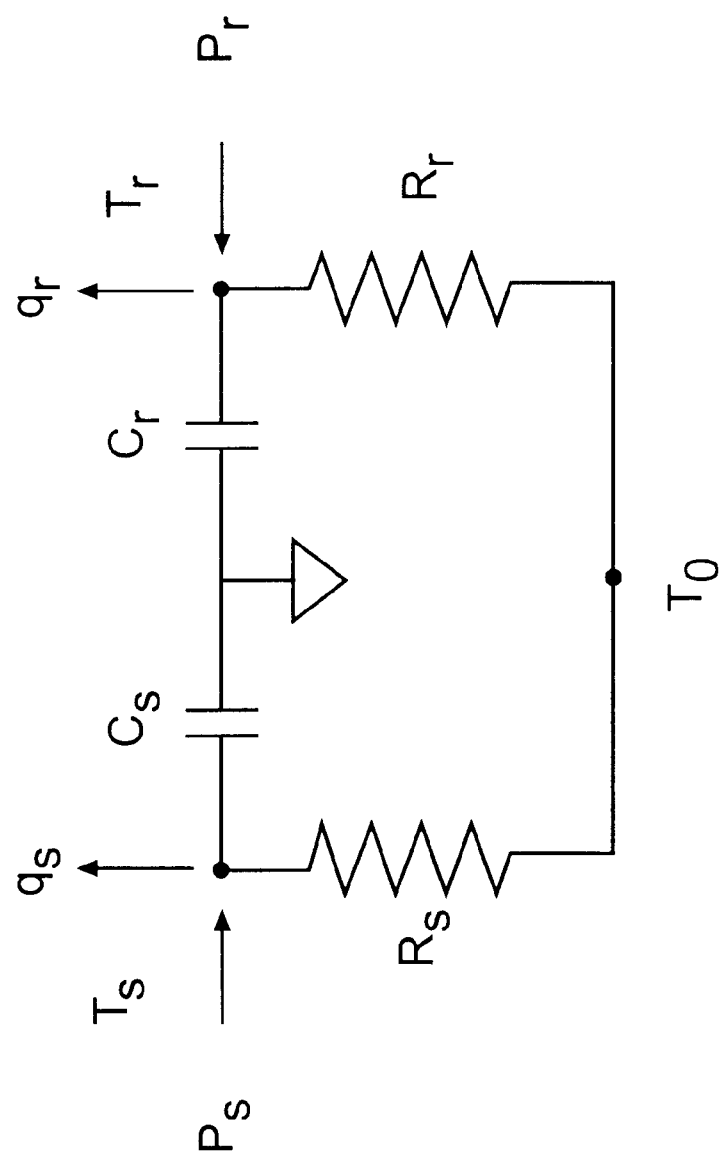
FIG. 2 is a thermal network model of a power compensation differential scanning calorimeter.
Figure 2A:
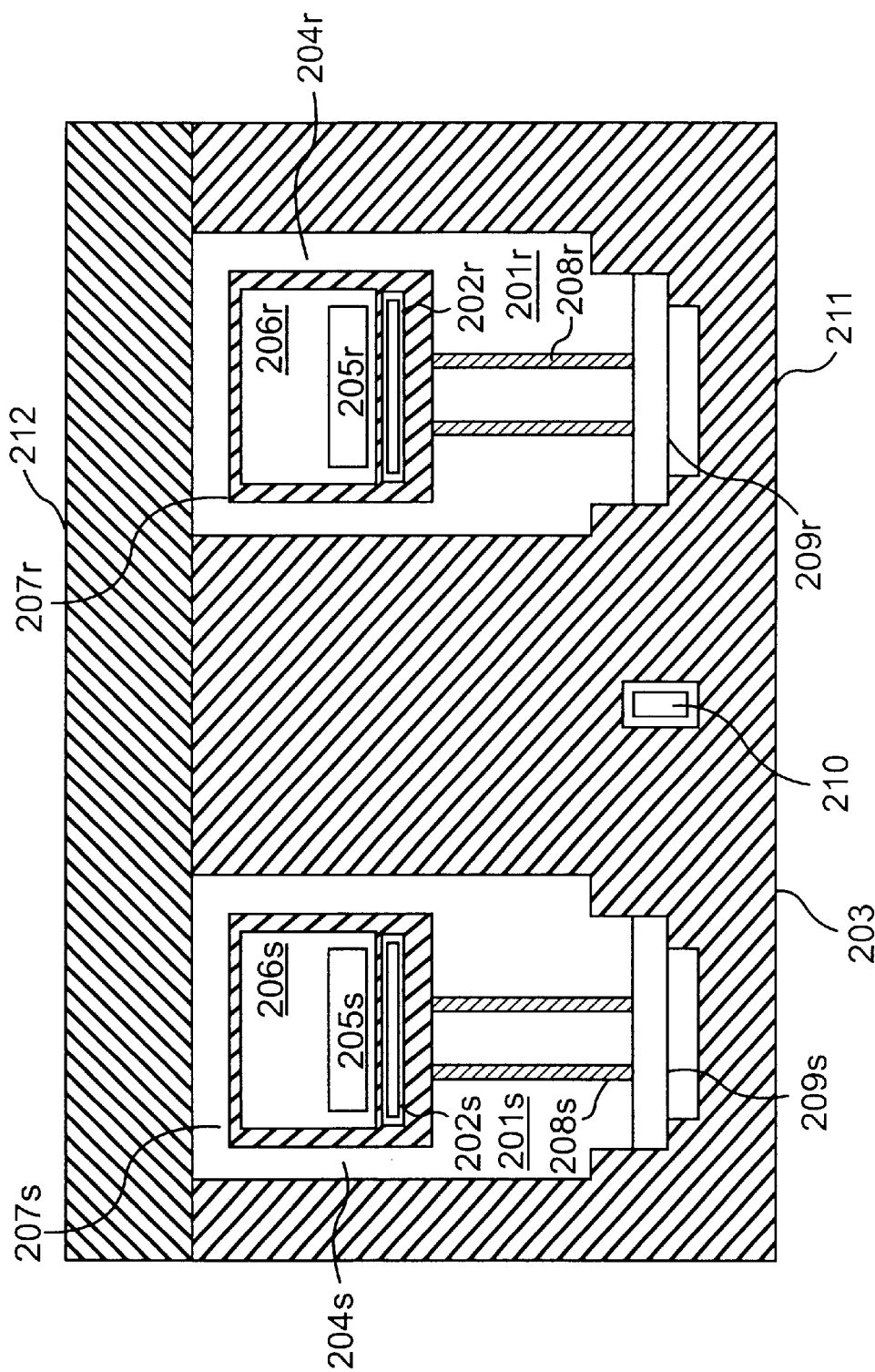
FIG. 2a is a schematic diagram of a power compensation DSC of an embodiment of the present invention.

FIG. 2a is a schematic diagram of a cross-sectional view of a power compensation DSC cell according to the power compensation embodiment of the present invention. The DSC cell comprises a sample holder assembly 201s and a reference holder assembly 201r installed in an isothermal enclosure 203. Overall, the sample and reference holder assemblies are manufactured to be as identical as possible. Sample holder 201s has a body 204s in which are embedded a temperature detector 202s, and a heating element (not shown in FIG. 2a). A sample in a sample pan 205s is inserted in the cavity 206s of the sample holder, which is closed by a lid 207s. The body of the sample holder 204s is supported by thermal resistor 208s, which is attached to flange 209s. The thermal resistor is the principal path for heat exchange between the sample holder and the isothermal enclosure and allows the sample holder to be heated to temperatures much higher than the isothermal enclosure by applying a modest quantity of heater power. Thermal resistor 208s is a tubular member with a small cross-sectional area in the direction normal to heat flow, as compared with its length in the direction of heat flow.

Similarly, reference holder 201r has a body 204r in which are embedded a temperature detector 202r, and a heating element (not shown in FIG. 2a). Reference pan 205r is inserted in the cavity 206r of reference holder 201r, which is closed by lid 207r. The body of the reference holder 204r is supported by thermal resistor 208r, which is attached to flange 209r. The thermal resistor is the principal path for heat exchange between the reference holder 201r and the isothermal enclosure, and allows the reference holder to be heated to temperatures much higher than the isothermal enclosure by modest heater power. It is a tubular member with a small cross-sectional area in the direction normal to heat flow as compared with its length in the direction of heat flow. A reference material could be placed in a reference pan 205r, which is inserted in the cavity of reference holder 201r, although the usual practice is to omit the reference material and place an empty pan 205r in reference holder 201r.

Isothermal enclosure 203 comprises a body 211 and a removable lid 212 that allows access to the sample and reference holders for loading the sample and reference. Flange 209s of the sample holder is joined to the body 211 of the isothermal enclosure so that heat flows from the sample holder and sample through the thermal resistor 208s to the isothermal body. Isothermal enclosure temperature detector 210 is installed in body 211 of the isothermal enclosure 203 to measure the isothermal temperature; the difference between this temperature and the temperature of the sample holder is $\Delta T_0$. The isothermal body is cooled by various means, for example a liquid cryogen, mechanical refrigeration, water or air. The isothermal enclosure is constructed of a high thermal conductivity material, typically aluminum, to minimize variation of temperature within the enclosure.

This embodiment of the present invention uses the sample temperature measurement as the only absolute temperature measurement. It also measures the differential temperature between the sample and reference holders, the differential temperature between the sample holder and the isothermal enclosure, and the differential power to the sample with respect to the reference. The differential power to the sample with respect to the reference is measured, for example, by measuring the power to the sample holder and the power to the reference holder separately, and obtaining the difference between the separate measurements. The power to the sample holder and the power to the reference holder can be measured in a number of different ways, for example by instrumentation that measures the voltages and currents to the sample and reference heaters. Thus, this embodiment uses a combination of a single absolute temperature measurement (the sample temperature), two differential temperature measurements (sample/reference and sample/enclosure) and a differential power measurement (sample/reference) to obtain the quantities needed to calculate the differential heat flow to the sample according to the power compensation DSC heat flow equation (equation 6, reproduced here for convenience):

$$q = \Delta p + \Delta T_0 \cdot \left(\frac{R_r - R_s}{R_r \cdot R_s}\right) - \frac{\Delta T}{R_r} + (C_r - C_s) \cdot \frac{dT_s}{d\tau} - C_r \cdot \frac{d\Delta T}{d\tau}$$

It will be recognized that other combinations of a single absolute temperature and two differential temperature measurements may also be used with a five term heat flow equation. The improvements of the current invention can also be obtained using the other configurations. There are three possible choices for the single absolute temperature measurement: the sample holder temperature, the reference holder temperature and the isothermal enclosure temperature. Each of these can be used with any two of the three possible differential temperature measurements to achieve the same results. Thus the sample temperature $T_s$ can be used as the absolute temperature measurement with differential temperature measurements $T_0-T_s$ and $T_s-T_r$ as in the preferred embodiment, or with $T_0-T_s$ and $T_0-T_r$ or with $T_s-T_r$ and $T_0-T_r$. The reference temperature $T_r$ can be used as the absolute temperature measurement with differential temperature measurements $T_s-T_r$ and $T_0-T_r$ or with $T_0-T_r$ and $T_0-T_s$ or with $T_s-T_r$ and $T_0-T_s$. The base temperature $T_0$ can be used as the absolute temperature measurement with $T_0-T_s$ and $T_s-T_r$, or with $T_0-T_s$ and $T_0-T_r$, or with $T_0-T_r$ and $T_s-T_r$. Thus, there are eight additional configurations that can give the same information if the five term heat flow equation is rewritten accordingly. All nine of the possible configurations are within the scope of the present invention.

Method for Determining Thermal Parameters

To use the five term Power Compensation DSC heat flow equation, the four thermal parameters $C_s$, $C_r$, $R_s$, $R_r$ must be determined. Determination of these parameters constitutes heat flow calibration of the DSC.

Heat flow calibration requires two experiments from which the four thermal parameters can be calculated. The first experiment is performed with an empty DSC cell. The DSC program begins with an isothermal temperature segment at a temperature below the lowest temperature of the desired calibration range, followed by a constant heating rate temperature ramp, and ending with an isothermal temperature segment above the highest temperature of the desired calibration range. The heating rate should be the same that is to be used for subsequent experiments. The second calibration experiment is performed, for example, with sapphire specimens without pans loaded in both the sample and reference holders. Other materials having known thermal properties and no transitions in the temperature range of interest may be used instead of sapphire. The same thermal program is used in the second experiment as was used for the first empty DSC experiment.

The heat balance equation on the sample side of a power compensation differential scanning calorimeter is:

$$q_s = \frac{T_0 - T_s}{R_s} + p_s - C_s \cdot \frac{dT_s}{d\tau}$$

On the reference side, the heat balance equation is:

$$q_r = \frac{T_0 - T_r}{R_r} + p_r - C_r \cdot \frac{dT_r}{d\tau}$$

Beginning with the heat balance equation for the sample side, the heat flow during the empty DSC experiment is set equal to zero, and the heat balance equation becomes:

$$\frac{\Delta T_{01}}{R_s} + p_{s1} - C_s \cdot \frac{dT_{s1}}{d\tau} = 0$$

The numerical subscript 1 indicates the first calibration experiment. For the second calibration experiment using sapphire specimens, the sample heat flow is set equal to:

$$q_{s2} = m_{s2} \cdot C_{sapph} \cdot \frac{dT_{s2}}{d\tau}$$

where $m_{s2}$ is the mass of the sapphire sample, $C_{sapph}$ is the known heat capacity of sapphire and the numerical subscript 2 indicates the second calibration experiment. For the second calibration experiment, the heat balance equation becomes:

$$\frac{\Delta T_{02}}{R_s} + p_{s2} - C_s \cdot \frac{dT_{s2}}{d\tau} = m_{s2} \cdot C_{sapph} \cdot \frac{dT_{s2}}{d\tau}$$

Solving these two equations simultaneously for $C_s$ and $R_s$ gives:

$$C_s = \frac{\Delta T_{01} \cdot \left(m_{s2} \cdot C_{sapph} \cdot \frac{dT_{s2}}{d\tau} - p_{s2}\right) + \Delta T_{02} \cdot p_{s1}}{\Delta T_{02} \cdot \frac{dT_{s1}}{d\tau} - \Delta T_{01} \cdot \frac{dT_{s2}}{d\tau}}$$

$$R_s = \frac{\Delta T_{02} \cdot \frac{dT_{s1}}{d\tau} - \Delta T_{01} \cdot \frac{dT_{s2}}{d\tau}}{\frac{dT_{s1}}{d\tau} \cdot \left(m_{s2} \cdot C_{sapph} \cdot \frac{dT_{s2}}{d\tau} - p_{s2}\right) + \frac{dT_{s2}}{d\tau} \cdot p_{s1}}$$

Similarly, the heat balance equations for the empty and the sapphire calibration runs on the reference side give:

$$\frac{T_{01} - T_{r1}}{R_r} + p_{r1} - C_r \cdot \frac{dT_{r1}}{d\tau} = 0$$

$$\frac{T_{02} - T_{r2}}{R_r} + p_{r2} - C_r \cdot \frac{dT_{r2}}{d\tau} = m_{r2} \cdot C_{sapph} \cdot \frac{dT_{r2}}{d\tau}$$

The reference temperature $T_r$ is not measured directly. Substituting for $T_r$ and for $\Delta T_0$:

$$T_r = T_s - \Delta T$$

$$\Delta T_0 = T_0 - T_s$$

The heat balance equations become:

$$\frac{\Delta T_{01} + \Delta T_1}{R_r} + p_{r1} - C_r \cdot \left(\frac{dT_{s1}}{d\tau} - \frac{d\Delta T_1}{d\tau}\right) = 0$$

$$\frac{\Delta T_{02} + \Delta T_2}{R_r} + p_{r2} - C_r \cdot \left(\frac{dT_{s2}}{d\tau} - \frac{d\Delta T_2}{d\tau}\right) = m_{r2} \cdot C_{sapph} \cdot \left(\frac{dT_{s2}}{d\tau} - \frac{d\Delta T_2}{d\tau}\right)$$

Simultaneous solution of these equations gives:

$$C_r = \frac{(\Delta T_{01} + \Delta T_1) \cdot \left[m_{r2} \cdot C_{sapph} \cdot \left(\frac{dT_{s2}}{d\tau} - \frac{d\Delta T_2}{d\tau}\right) - p_{r2}\right] + (\Delta T_{02} + \Delta T_2) \cdot p_{r1}}{(\Delta T_{01} + \Delta T_1) \cdot \left(\frac{d\Delta T_2}{d\tau} - \frac{dT_{s2}}{d\tau}\right) + (\Delta T_{02} + \Delta T_2) \cdot \left(\frac{dT_{s1}}{d\tau} - \frac{d\Delta T_1}{d\tau}\right)}$$

$$R_r = \frac{(\Delta T_{01} + \Delta T_1) \cdot \left(\frac{d\Delta T_2}{d\tau} - \frac{dT_{s2}}{d\tau}\right) + (\Delta T_{02} + \Delta T_2) \cdot \left(\frac{dT_{s1}}{d\tau} - \frac{d\Delta T_1}{d\tau}\right)}{\left[m_{r2} \cdot C_{sapph} \cdot \left(\frac{dT_{s1}}{d\tau} - \frac{d\Delta T_1}{d\tau}\right) - p_{r2}\right] \cdot \left(\frac{dT_{s1}}{d\tau} - \frac{d\Delta T_1}{d\tau}\right) - p_{r1} \cdot \left(\frac{d\Delta T_2}{d\tau} - \frac{dT_{s2}}{d\tau}\right)}$$

In an alternate embodiment, both calibration experiments may contain specimens. The specimens in the two calibration experiments must have substantially different masses. For example, the sample (reference) specimen masses are substantially different if the mass of the sample (reference) specimen for the first calibration experiment is twice the mass of the sample (reference) specimen for the second experiment, whereas a 5% difference would not be substantial. In this embodiment, the heat balance equation for the first experiment on the sample side becomes:

$$\frac{\Delta T_{01}}{R_s} + p_{s1} - C_s \cdot \frac{dT_{s1}}{d\tau} = m_{s1} \cdot C_{sapph} \cdot \frac{dT_{s1}}{d\tau}$$

and the heat balance equation for the first experiment on the reference side becomes:

$$\frac{\Delta T_{01} + \Delta T_1}{R_r} + p_{r1} - C_r \cdot \left(\frac{dT_{s1}}{d\tau} - \frac{d\Delta T_1}{d\tau}\right) = m_{r1} \cdot C_{sapph} \cdot \left(\frac{dT_{s1}}{d\tau} - \frac{d\Delta T_1}{d\tau}\right)$$

Solving simultaneously as before gives:

$$C_s = \frac{\Delta T_{01} \cdot \left(m_{s2} \cdot C_{sapph} \cdot \frac{dT_{s2}}{d\tau} - p_{s2}\right) + \Delta T_{02} \cdot \left(p_{s1} - m_{s1} \cdot C_{sapph} \cdot \frac{dT_{s1}}{d\tau}\right)}{\Delta T_{02} \cdot \frac{dT_{s1}}{d\tau} - \Delta T_{01} \cdot \frac{dT_{s2}}{d\tau}}$$

$$R_s = \frac{\Delta T_{02} \cdot \frac{dT_{s1}}{d\tau} - \Delta T_{01} \cdot \frac{dT_{s2}}{d\tau}}{\frac{dT_{s1}}{d\tau} \cdot \left(m_{s2} \cdot C_{sapph} \cdot \frac{dT_{s2}}{d\tau} - p_{s2}\right) + \frac{dT_{s2}}{d\tau} \cdot \left(p_{s1} - m_{s1} \cdot C_{sapph} \cdot \frac{dT_{s1}}{d\tau}\right)}$$

$$C_r = \frac{(\Delta T_{01} + \Delta T_1) \cdot \left[m_{r2} \cdot C_{sapph} \cdot \left(\frac{dT_{s2}}{d\tau} - \frac{d\Delta T_2}{d\tau}\right) - p_{r2}\right] + (\Delta T_{02} + \Delta T_2) \cdot \left[p_{r1} - m_{r1} \cdot C_{sapph} \cdot \left(\frac{dT_{s1}}{d\tau} - \frac{d\Delta T_1}{d\tau}\right)\right]}{(\Delta T_{01} + \Delta T_1) \cdot \left(\frac{d\Delta T_2}{d\tau} - \frac{dT_{s2}}{d\tau}\right) + (\Delta T_{02} + \Delta T_2) \cdot \left(\frac{dT_{s1}}{d\tau} - \frac{d\Delta T_1}{d\tau}\right)}$$

$$R_r = \frac{(\Delta T_{01} + \Delta T_1) \cdot \left(\frac{d\Delta T_2}{d\tau} - \frac{dT_{s2}}{d\tau}\right) + (\Delta T_{02} + \Delta T_2) \cdot \left(\frac{dT_{s1}}{d\tau} - \frac{d\Delta T_1}{d\tau}\right)}{\left(\frac{dT_{s1}}{d\tau} - \frac{d\Delta T_1}{d\tau}\right) \cdot \left[m_{r2} \cdot C_{sapph} \cdot \left(\frac{dT_{s2}}{d\tau} - \frac{d\Delta T_2}{d\tau}\right) - p_{r2}\right] + \left(\frac{dT_{s2}}{d\tau} + \frac{d\Delta T_2}{d\tau}\right) \cdot \left[p_{r1} - m_{r1} \cdot C_{sapph} \cdot \left(\frac{dT_{s1}}{d\tau} - \frac{d\Delta T_1}{d\tau}\right)\right]}$$

The thermal capacitances and resistances are used to calculate sample heat flow during a DSC experiment. They may be used as tabular data, with suitable interpolation for intermediate values, or they may be fitted by a mathematical expression, e.g., to a polynomial. In either case, the calculated capacitances and resistances must be applied as a function of temperature. The sapphire specimen masses range from 25 mg to 125 mg, with typical masses ranging from 75 mg to 100 mg.

The power to the sample $p_s$ and the power to the reference $p_r$ are measured separately during the calibration step. The differential power is obtained by subtracting $p_r$ from $p_s$.

Improved Calculation

A power compensation DSC as described above comprises independent sample and reference holders that may be modeled using a thermal resistance and a thermal capacitance for each of the sample and reference holders as shown in FIG. 2. Thermal resistance and capacitance elements are idealizations of the sample and reference holders, which allow simple mathematical expressions describing the thermal behavior of the DSC to be written. $R_s$ and $R_r$ are thermal resistances, $C_s$ and $C_r$ are thermal capacitances representing the sample and reference holders. $T_0$, $T_s$ and $T_r$ are the temperatures of the isothermal enclosure, sample holder and reference holder. Heating power supplied to the sample holder is $p_s$, comprising the average heating power plus the differential power. Heating power supplied to the reference holder is $p_r$, comprising the average heating power minus the differential power. The heat flow to the sample and its pan and to the reference and its pan are $q_s$ and $q_r$.

Performing a heat balance on the sample and reference gives the heat flow differential equations, $$q_s = \frac{T_0 - T_s}{R_s} + p_s - C_s \cdot \frac{dT_s}{d\tau}$$

$$q_r = \frac{T_0 - T_r}{R_r} + p_r - C_r \cdot \frac{dT_r}{d\tau}$$

In the preferred embodiment of the invention disclosed in the '949 application, temperature $T_0$, the difference between the isothermal enclosure and sample holder temperatures and the difference between the sample and reference holder temperatures are measured. The differential temperatures are defined by:

$$\Delta T = T_s - T_r, \Delta T_0 = T_0 - T_s$$

Substituting into the heat balance equations gives, $$q_s = \frac{\Delta T_0}{R_s} + p_s - C_s \cdot \frac{dT_s}{d\tau} \text{ and}$$

$$q_r = \frac{\Delta T_0 + \Delta T}{R_r} + p_r - C_r \cdot \left(\frac{dT_s}{d\tau} - \frac{d\Delta T}{d\tau}\right)$$

Sample temperature is obtained from the definition of $\Delta T_0$, $$T_s = T_0 - \Delta T_0$$

Thermal resistances and capacitances of the sample and reference holders as a function of temperature are obtained using the calibration method disclosed above and in the '949 application. Using thermal resistances and capacitances from calibration with the sample and reference holder power, temperatures and differential temperatures measured during a DSC experiment allows the sample and reference heat flow, $q_s$ and $q_r$ to be found. The difference between sample and reference heat flows is the desired result:

$$q = q_s - q_r$$

As noted above, the sample and reference heat flows include the heat flow to the sample and reference and to their pans.

$$q_s = q_{ss} + q_{ps} \quad q_r = q_{rs} + q_{pr}$$

Where $q_{ss}$ is the sample heat flow, $q_{ps}$ is the sample pan heat flow, $q_{rs}$ is the reference heat flow and $q_{pr}$ is the reference pan heat flow. The pans and the reference do not have transitions so that their heat flows are just the sensible heat associated with their specific heats:

$$q_{ps} = m_{ps} \cdot c_p \cdot \frac{dT_{ps}}{d\tau} \quad q_r = m_{pr} \cdot c_p \cdot \frac{dT_{pr}}{d\tau} + m_{rs} \cdot c_{rs} \cdot \frac{dT_{pr}}{d\tau}$$

Where $m_{ps}$ and $m_{pr}$ are the masses of the sample and reference pans, $c_p$ is the specific heat of the pan material, $m_{rs}$ is the mass of the reference material, $c_{rs}$ is the specific heat of the reference material. The sample pan temperature is $T_{ps}$ and the reference pan temperature is $T_{pr}$. It is assumed that the reference material has no transitions and it heats at the same rate as the reference pan.

Substituting for the sample pan heat flow and solving for the sample heat flow:

$$q_{ss} = q_s - m_{ps} \cdot c_p \cdot \frac{dT_{ps}}{d\tau}$$

Solving the reference heat flow equation for the pan specific heat and substituting it into the sample heat flow equation:

$$q_{ss} = q_s - q_r \cdot \frac{m_{ps}}{m_{pr}} \cdot \frac{\frac{dT_{ps}}{d\tau}}{\frac{dT_{pr}}{d\tau}} + \frac{m_{ps}}{m_{pr}} \cdot m_{rs} \cdot c_{rs} \cdot \frac{dT_{ps}}{d\tau}$$

This equation gives the actual sample heat flow, accounting for the sample and reference pan heat flows and the heat flow to the reference. The second term on the right hand side is seen to be the reference heat flow multiplied by the ratio of the sample and reference pan masses and by the ratio of the sample and reference pan heating rates. It accounts for the fact that during a transition, the sample pan heats at a different rate than the reference pan because of the transition heat flow. The third term accounts for the heat flow to the reference material. In most cases, the reference pan is empty and the sample heat flow equation becomes:

$$q_{ss} = q_s - q_r \cdot \frac{m_{ps} \cdot \frac{dT_{ps}}{d\tau}}{m_{pr} \cdot \frac{dT_{pr}}{d\tau}}$$

Both of these equations can be written using different nomenclature, or using different units, or using different, but thermodynamically equivalent algebraic expressions.

When the sample heating rate is different from the reference heating rate, the fraction of reference heat flow subtracted from the sample heat flow is greater or less, depending upon whether the sample pan heating rate is greater or less than that of the reference pan. Because the reference heat flow is just the reference pan heat flow, this equation accounts for differences between sample and reference pan heating rates. For example, during a melt in DSC, the sample pan heating rate falls below the programmed rate, while the reference pan continues to heat at the programmed rate. In a conventional DSC the reference heat flow being subtracted from the sample heat flow is for a pan heating at the programmed rate thus, during the melt too much heat is being subtracted from the sample heat flow and the heat flow signal is too small. During the baseline return, the sample pan is heating faster than the reference pan and insufficient heat flow is subtracted from the sample heat flow, consequently the heat flow signal is too large.

To use the true sample heat flow equation requires that the sample and reference pan temperatures be known so that their derivatives may be taken. Unfortunately there is no way to measure the pan temperatures directly. The pan temperatures can be calculated using the temperature and heat flow signals.

The equations for heat flow from the sample and reference holders to the sample and reference pans are:

$$q_s = \frac{T_s - T_{ps}}{R_{ps}} \quad q_r = \frac{T_r - T_{pr}}{R_{pr}}$$

Solving for the pan temperatures:

$$T_{ps} = T_s - q_s \cdot R_{ps} \quad T_{pr} = T_r - q_r \cdot R_{pr}$$

Using these equations, the pan temperatures and sample heat flows are obtained from measurements. $R_{ps}$ and $R_{pr}$ can be determined using the semi-empirical procedures described above for these parameters with reference to heat flux calorimeters.

Experimental Results

Figure 3:
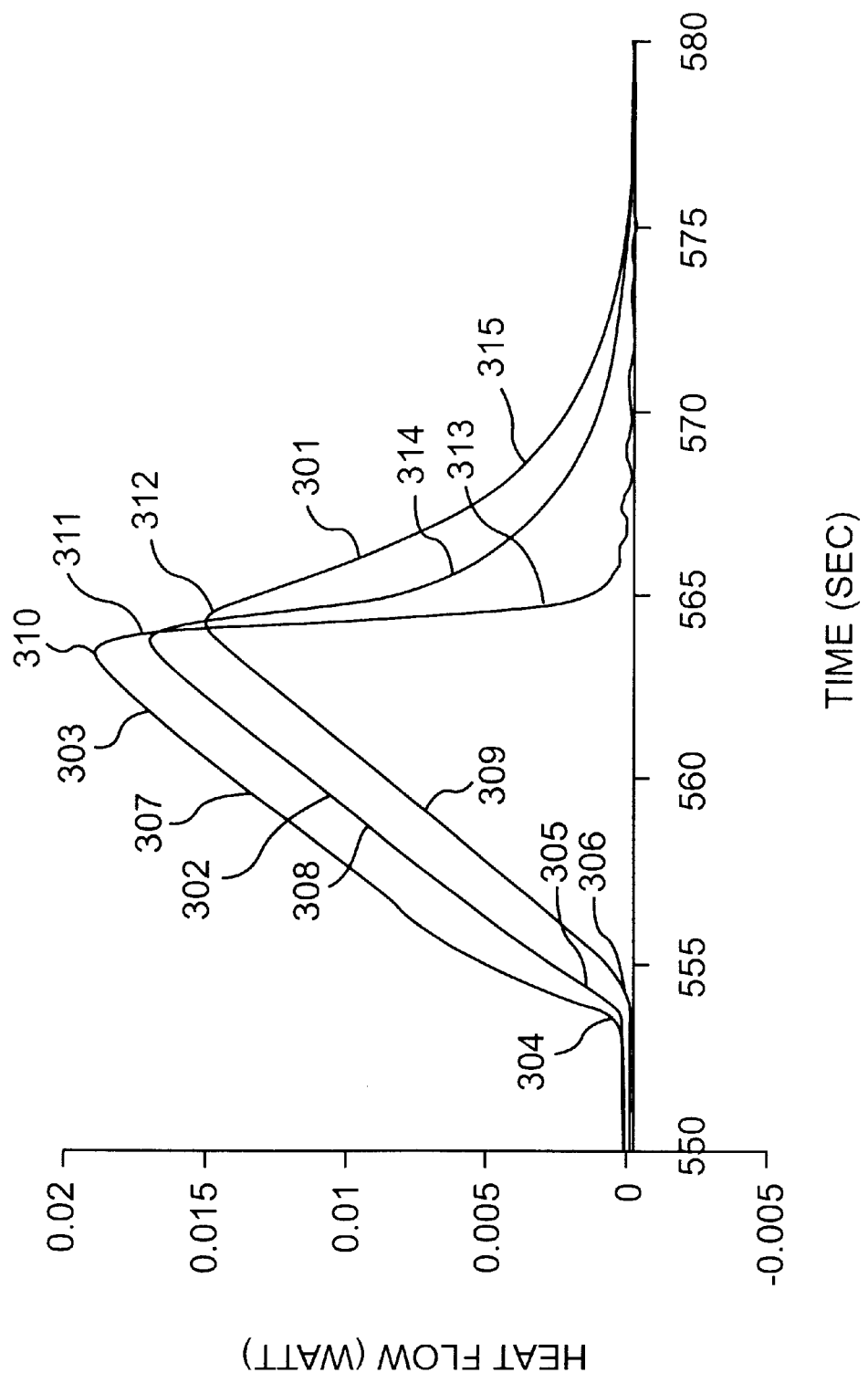
FIG. 3 is a plot showing a comparison of the heat flow obtained according to the present invention using the improved calculation described below (curve 3) to the heat flow obtained using conventional DSCs (curve 1), and to the heat flow obtained using the present invention without the improved calculation (curve 2).

FIG. 3 shows the application of the improved calculation of the present invention to the calculation of DSC heat flows in a heat flux DSC, for a 4.92 mg indium melt at 10° C./min plotted versus time. The conventional DSC result is the curve labeled 301, the result using the present invention without using the improved calculation is labeled 302 and the result using the method of the present invention using the improved calculation is labeled 303. Beginning at the left side of the plot, the onset of the indium melt calculated using the improved calculation 304 occurs earlier and is steeper than the onset of indium that occurs using the present invention without using the improved calculation 305, or using a conventional DSC 306. During the melt, the heat flow signal calculated using the improved calculation 307 is much larger than that obtained using the present invention without using the improved calculation 308, which in turn is substantially larger than the signal obtained using conventional DSC 309. The melt is completed at the heat flow signal peak when the latent heat of fusion has been absorbed by the sample.

The heat flow calculated using the improved calculation 310 is higher and occurs slightly earlier compared to the peak calculated according to the present invention without using the improved calculation 311, and much higher and earlier still than the peak obtained using a conventional DSC 312. Immediately following the peak, the sample heat flow decreases rapidly as the flow of heat to the sample following the melt returns to the value just before the transition which, corresponds to the specific heat of the sample. The post melt decay of the heat flow signal 313 calculated using the improved calculation of the present invention is extremely rapid, while the post melt heat flow decay 314 using the present invention without using the improved calculation is somewhat slower and the post melt decay 315 of conventional DSC is slower still. The complete indium melt heat flow signal 303 calculated using the improved calculation comprising the onset 304, melt 307, peak heat flow 310 and post melt decay 313 is a much more accurate measurement than that according to the present invention without using the improved calculation (as shown in curve 302), or of a conventional DSC (as shown in curve 301).

Modulated Differential Scanning Calorimetry

As described above, the apparatus of the present invention measures two temperature difference signals: $\Delta T$ (the difference between the temperatures of the sample and reference positions of the sensor) and $\Delta T_0$ (the difference between the temperatures of the sample position and the base of the sensor. To carry out an MDSC experiment, the temperature of the DSC cell in the differential scanning calorimeter is varied according to a temperature program characterized by having a periodic modulation function (e.g., a sinusoidal, a triangular wave, a sawtooth, a square wave, or any combination of the above) superimposed upon a linear ramp (characterized by a constant heating rate or cooling rate).

Most differential scanning calorimeter experiments are carried out with a sample in a sample pan, and with an empty reference pan, although in some cases the reference pan may actually contain a reference material. The following equations must be understood as covering both the case when the reference pan has a reference material in it, and the case when the reference pan is empty.

The sample and reference heat flow signals are given by:

$$q_s = \frac{\Delta T_0}{R_s} - C_s \cdot \frac{dT_s}{d\tau} \qquad q_r = \frac{\Delta T_0 + \Delta T}{R_r} - C_r \cdot \left(\frac{dT_s}{d\tau} - \frac{d\Delta T}{d\tau}\right)$$

where the thermal resistances and capacitances, $R_s$, $R_r$, $C_s$ and $Cr$ of the sensor are determined as described above.

The sample pan temperature $T_{ps}$ and the reference pan temperature $T_{pr}$ are:

$$T_{ps} = T_s - q_s \cdot R_{ps} \quad T_{pr} = T_r - q_r \cdot R_{pr}.$$

The sample and reference heat flows and temperatures, and sample pan and reference pan temperatures are deconvoluted independently, using the algorithm described in U.S. Pat. No. 5,224,775 (the "'775 patent").

The apparent heat capacities for the sample and reference (apparent because these terms include the heat capacities of the pans as well as the heat capacities of the sample and/or reference) are calculated using:

$$C_{sa} = \frac{\tilde{q}_s}{\omega \cdot \tilde{T}_{ps}} \qquad C_{ra} = \frac{\tilde{q}_r}{\omega \cdot \tilde{T}_{pr}}$$

The ~ indicates the amplitude of the heat flow or temperature as calculated using the MDSC deconvolution algorithm disclosed in the '775 patent; $\omega$ is the cyclic frequency of the modulation $2\pi$ divided by the modulation period).

The measured nonreversing sample and reference heat flows are calculated as follows:

$$q_{sn} = \overline{q_s} - C_{sa} \cdot \frac{d\overline{T_{ps}}}{d\tau} \qquad q_{rn} = \overline{q_r} - C_{ra} \cdot \frac{d\overline{T_{pr}}}{d\tau}$$

where the quantities with an overbar are averaged over one period, as described in the '775 patent.

The differential reversing heat capacity is calculated from:

$$C_{prev} = C_{sa} - \frac{m_{ps}}{m_{pr}} \cdot C_{ra}$$

The differential reversing heat flow, the differential nonreversing heat flow and the differential total heat flow are calculated from:

$$q_{rev} = C_{prev} \cdot \frac{d\overline{T_{ps}}}{d\tau}$$

The differential nonreversing heat capacity is calculated from:

$$C_{pnon} = \frac{q_{non}}{\frac{d\overline{T_{ps}}}{d\tau}}$$

and the differential total heat capacity is calculated from:

$$C_p = C_{prev} + C_{pnon}$$

Figure 4:
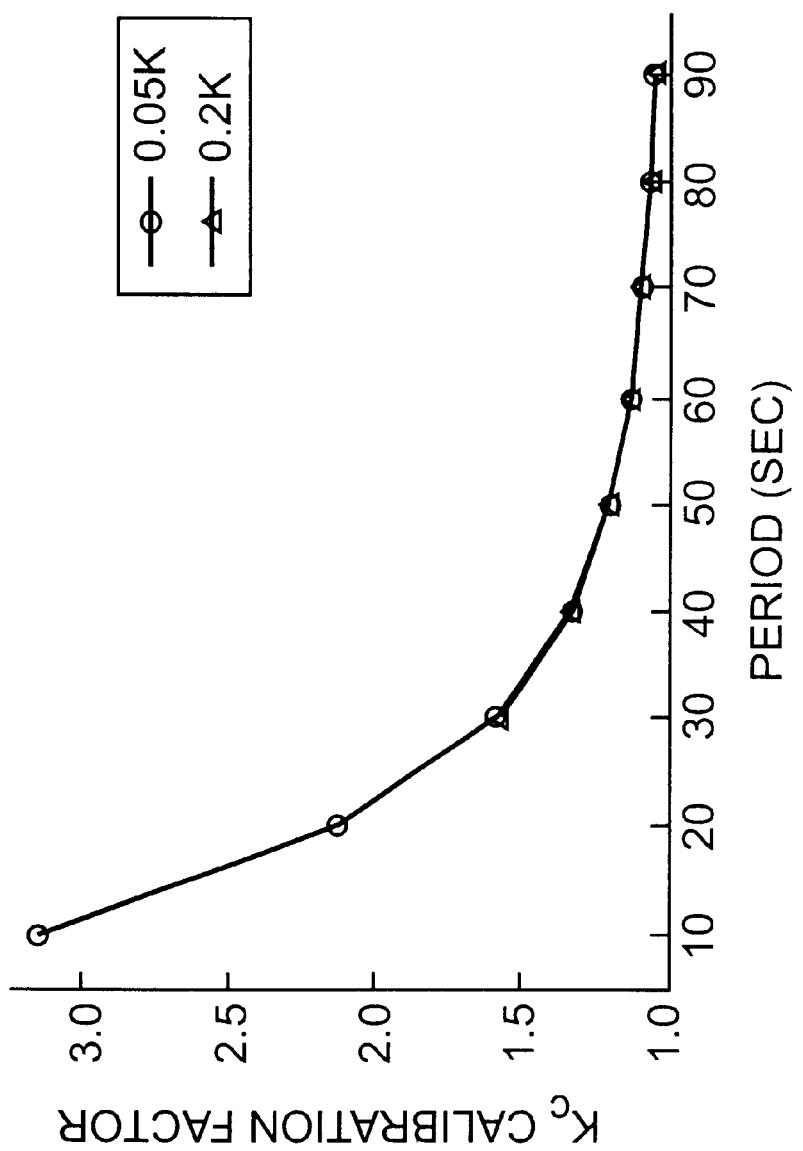
FIG. 4 is a mathematical simulation showing the dependence of the calibration factor on period when the present invention is not used.
Figure 5A:
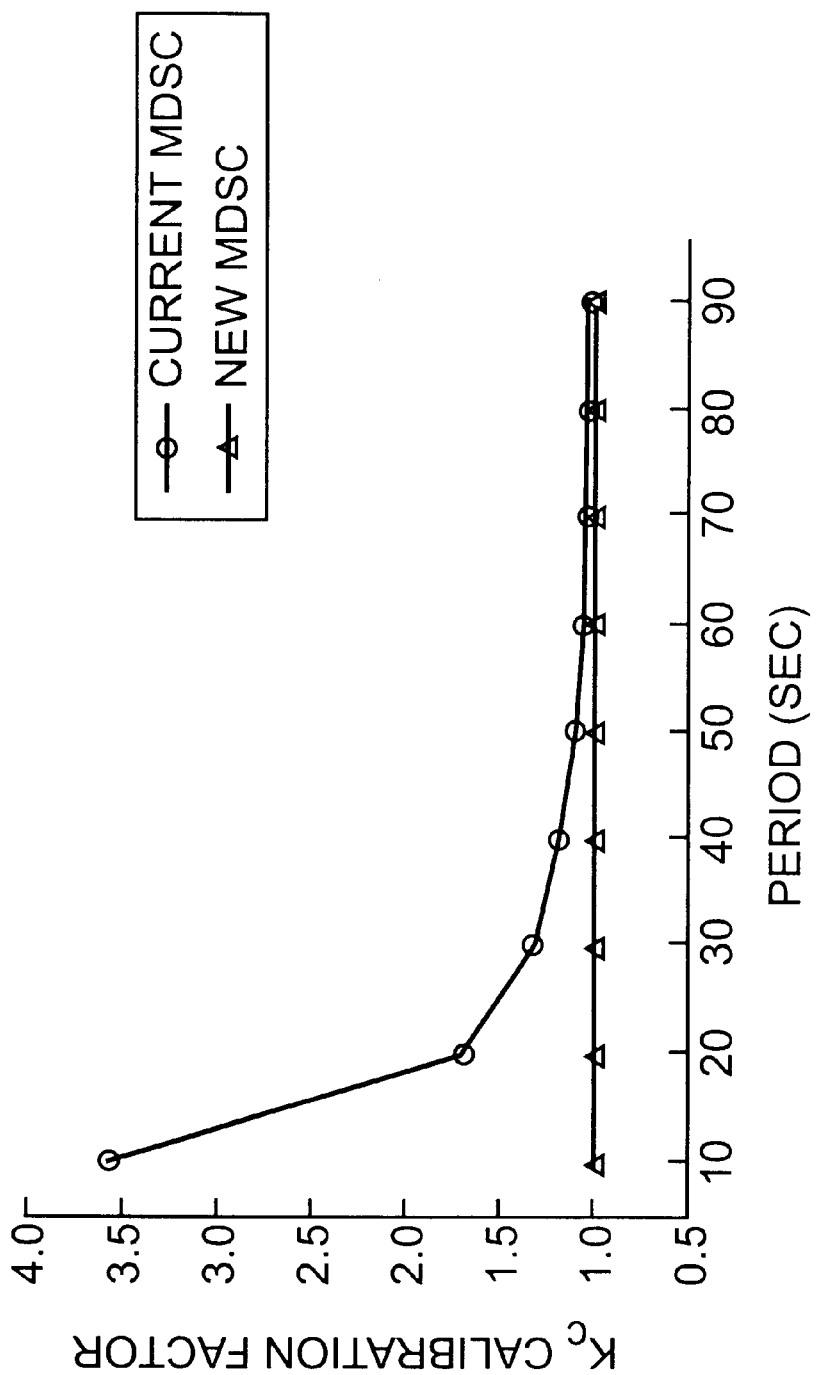
FIGS. 5a and 5b are a mathematical simulation and the results of an actual experiment, respectively, comparing the calibration factor required to practice MDSC without the present invention (circles) to the calibration factor using the present invention (triangles).

FIG. 5a shows the result of a mathematical simulation of heat capacity measurement by MDSC using the DSC of the '949 application, for a sample having a heat capacity of 0.005 joule/°C. The heat capacity calibration factor is determined by dividing the correct heat capacity by the value calculated from the model temperature and heat flow amplitudes using the MDSC method without using the present invention and the method of the present invention. The result obtained without using the present invention is labeled Current MDSC, and the method of the present invention is labeled New MDSC. Comparing the two results, the Current MDSC result shows $C_p$ calibration factors that become very large as period decreases, similar to the curve of FIG. 4, whereas the New MDSC curve obtained using the present invention gives calibration factors that are very close to 1.0, and that are almost constant as a function of the period of the modulation.

Figure 5B:
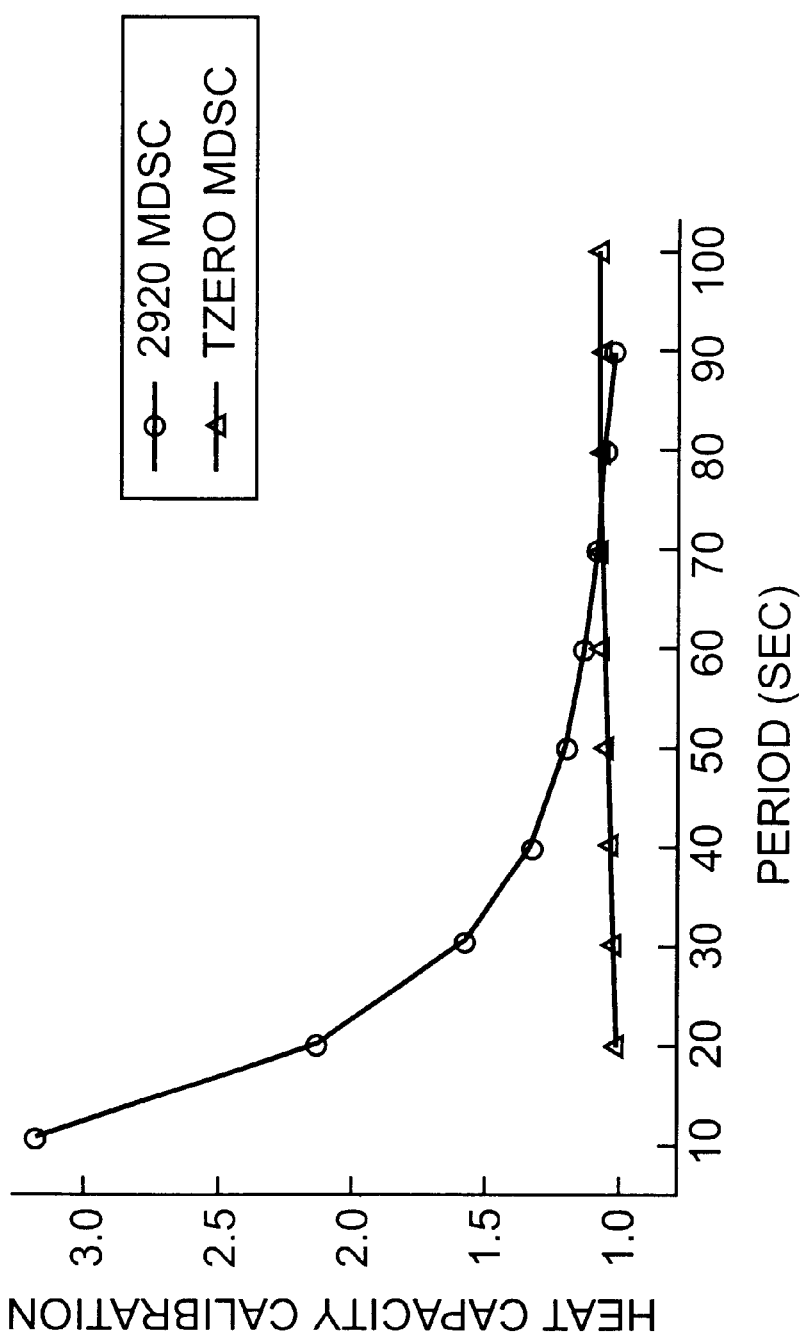

The results of the numerical simulation were confirmed in an actual experiment. FIG. 5b is a comparison the dependency of the measured heat capacity calibration factor on period for the apparatus of the '775 patent (the curve with the circles, labeled 2920 MDSC) to the dependency of the measured calibration factor according to the present invention (the curve with triangles, labeled Tzero MDSC).

U.S. Pat. No. 5,599,104 to Nakamura et al. (the '104 patent) discloses a method of calculating heat flow from a MDSC experiment that also uses separate sample and reference heat flow signals. The equation for heat capacity used is:

$$\Delta C_p = \frac{\overline{q_s} - \overline{q_r}}{\omega \cdot T},$$

where the sample and reference heat flow signals are obtained by measuring two differential temperatures, one on each of the sample and reference sides of the DSC. Heat flow is calculated using the equations:

$$q_s = \frac{\Delta T_s}{R} \quad q_r = \frac{\Delta T_r}{R}$$

It is assumed that the DSC sensor is perfectly balanced and the effects of heat storage in the sensor are ignored.

The inventors of the '104 patent clearly recognized the need to separate sample and reference heat flows, since they noted that they have different amplitude and phase angle. However, they apparently failed to recognize that the sample and reference temperatures also have different amplitude and phase angle. Also, the temperature $T_s$ that is used is the DSC sample sensor temperature. Consequently, sample heat capacity that is found using this method will also require large heat capacity calibration factors that are strongly dependent on modulation period, just as in the method disclosed in U.S Pat. No. 5,224,775.

The foregoing disclosure of embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

What is claimed is:

1. A method for calculating a total differential heat flow to a sample with respect to a reference in a modulated differential scanning calorimeter having a sensor comprising an absolute temperature measurement detector for measuring a temperature of a base position on the sensor, a first differential temperature detector for measuring a temperature difference between a sample position and the base position, and a second differential temperature detector for measuring a temperature difference between a reference position and the sample position, comprising:
   (a) the step of operating the differential scanning calorimeter;
   (b) the step of obtaining a sample signal and a reference signal;
   (c) the step of deconvoluting the sample signal;
   (d) the step of deconvoluting the reference signal; and
   (e) the step of calculating the total differential heat flow to the sample.

2. The method of claim 1, comprising the step of calculating a differential reversing heat flow to the sample.

3. The method of claim 1, comprising the step of calculating a differential nonreversing heat flow to the sample.

4. The method of claim 1, comprising the step of calculating a differential reversing heat capacity of the sample.

5. The method of claim 1, further comprising the step of calculating a differential nonreversing heat capacity of the sample.

6. The method of claim 1, further comprising the step of calculating a differential heat capacity of the sample.

7. The method of claim 1, comprising the step of calculating an apparent heat capacity of the sample.

8. The method of claim 1, comprising averaging a term representative of heat flow to the sample pan over one period.

9. The method of claim 1, comprising using a deconvolution algorithm to calculate a heat flow amplitude.

10. The method of claim 1, comprising using a deconvolution algorithm to calculate a temperature amplitude.

11. The method of claim 1, further comprising calculating the differential heat capacity from:

$$C_p = C_{prev} + C_{pnon}$$

where:

$$C_{prev} = C_{sa} - \frac{m_{ps}}{m_{pr}} \cdot C_{ra}$$

and $$C_{pnon} = \frac{q_{non}}{\frac{d\overline{T_{ps}}}{d\tau}}.$$

12. The method of claim 1, wherein the step of calculating the differential total heat flow comprises calculating:

$$q_{tot} = q_{rev} + q_{non}$$

where:

$$q_{rev} = C_{prev} \cdot \frac{d\overline{T_{ps}}}{d\tau},$$

$$q_{non} = q_{sn} - q_{rn},$$

$$q_{sn} = \overline{q_s} - C_{sa} \cdot \frac{d\overline{T_{ps}}}{d\tau},$$

and $$q_{rn} = \overline{q_r} - C_{ra} \cdot \frac{d\overline{T_{pr}}}{d\tau}.$$

13. The method of claim 1, comprising calculating a differential reversing heat flow from:

$$q_{rev} = C_{prev} \cdot \frac{d\overline{T_{ps}}}{d\tau}.$$

14. The method of claim 1, comprising calculating a differential nonreversing heat flow from:

$$q_{non} = q_{sn} - q_{rn},$$

where $$q_{sn} = \overline{q_s} - C_{sa} \cdot \frac{d\overline{T_{ps}}}{d\tau},$$

and $$q_{rn} = \overline{q_r} - C_{ra} \cdot \frac{d\overline{T_{pr}}}{d\tau}.$$

15. A method for calculating the reversing heat capacity of a sample from data obtained using a modulated differential scanning calorimeter comprising a differential scanning calorimeter cell having an independent sample measuring section and an independent reference measuring section comprising:

(a) varying a temperature of the differential scanning calorimeter cell according to a temperature program characterized by a periodic component superimposed upon a linear ramp;

(b) measuring a temperature of a sample pan in the sample measuring section and a temperature of a reference pan in the reference measuring section (c) measuring a heat flow to the sample and sample pan and heat flow to a reference material, when the reference is used, and to the reference pan;

(d) deconvoluting the temperature of the sample pan and the temperature of the reference pan to obtain an amplitude of the temperature of the sample pan and an amplitude of the temperature of the reference pan;

(e) deconvoluting the heat flow to the sample and sample pan and the heat flow to the reference material, when the reference material is used, and to the reference pan to obtain an amplitude of the heat flow to the sample and sample pan and an amplitude of the heat flow to the reference material, when the reference material is used, and to the reference pan;

(f) calculating an apparent heat capacity for the sample and for the reference material;

(g) calculating a nonreversing heat flow to the sample and sample pan and a nonreversing heat flow to the reference material, when the reference material is used, and to the reference pan; and (h) calculating a differential reversing heat capacity of the sample from the apparent heat capacity of the sample and the apparent heat capacity of the reference material.

16. The method of claim 15, further comprising calculating a differential reversing heat flow to the sample.

17. The method of claim 15, further comprising calculating a differential nonreversing heat flow to the sample.

18. The method of claim 15, further comprising calculating the total differential heat flow to the sample.

19. The method of claim 15, further comprising calculating a differential nonreversing heat capacity of the sample.

20. The method of claim 15, further comprising calculating a differential total heat capacity of the sample.

21. The method of claim 15, wherein the apparent heat capacity for the sample and for the reference are calculated using:

$$C_{sa} = \frac{\tilde{q}_s}{\omega \cdot \tilde{T}_{ps}} \text{ and } C_{ra} = \frac{\tilde{q}_r}{\omega \cdot \tilde{T}_{pr}}.$$

22. The method of claim 21, wherein the nonreversing heat flow to the sample pan and the nonreversing heat flow to the reference pan are calculated using:

$$q_{sn} = \overline{q_s} - C_{sa} \cdot \frac{d\overline{T_{ps}}}{d\tau} \text{ and } q_{rn} = \overline{q_r} - C_{ra} \cdot \frac{d\overline{T_{pr}}}{d\tau}$$

respectively.

23. The method of claim 21, wherein the differential reversing heat capacity of the sample is calculated from:

$$C_{prev} = C_{sa} - \frac{m_{ps}}{m_{ps}} \cdot C_{ra}.$$

24. The method of claim 23, further comprising calculating a differential reversing heat flow, a differential nonreversing heat flow and a total heat flow using:

$$q_{rev} = C_{prev} \cdot \frac{d\overline{T_{ps}}}{d\tau}$$

$$q_{non} = q_{sn} - q_{rn}$$

$$q_{tot} = q_{rev} + q_{non}.$$

25. The method of claim 24, further comprising calculating a differential nonreversing heat capacity and a differential total heat capacity from:

$$C_{pnon} = \frac{q_{non}}{\frac{d\overline{T_{ps}}}{d\tau}}$$

and the differential total heat capacity is calculated from:

$$C_p = C_{prev} + C_{pnon}.$$

26. A differential scanning calorimeter having a DSC cell comprising:

(a) an absolute temperature detector for measuring a temperature of a base position on a sensor;

(b) a first differential temperature detector for measuring a temperature difference between a sample position and the base position, said sample position having a sample and a sample pan thereon;

(c) a second differential temperature detector for measuring a temperature difference between a reference position and the sample position, said reference position having a reference material, when a reference material is used, and a reference pan thereon;

(d) means for varying a temperature of the DSC cell according to a temperature program characterized as having a periodic modulation superimposed on a linear ramp;

(e) means for measuring a signal representative of heat flow to the sample and sample pan and means for measuring a signal representative of heat flow to the reference material, when the reference material is used, and reference pan as the temperature of the DSC cell is varied according to the temperature program;

(f) means for deconvoluting the signal representative of heat flow to the sample and sample pan, means for deconvoluting the signal representative of heat flow to the reference material, when the reference material is used, and to the reference pan, means for deconvoluting a signal representative of the temperature of the sample pan, and means for deconvoluting a signal representative of the temperature of the reference pan; and (g) means for calculating a differential reversing heat capacity.

27. The differential scanning calorimeter of claim 26, wherein the means for calculating the differential reversing heat capacity calculates the apparent heat capacities for the sample and the reference.

28. The differential scanning calorimeter of claim 27, comprising means for calculating a nonreversing sample heat flow.

29. The differential scanning calorimeter of claim 26, further comprising means for calculating a differential nonreversing heat flow, a differential reversing heat flow, and a differential total heat flow.

30. The differential scanning calorimeter of claim 26, further comprising means for calculating a differential nonreversing heat capacity.

31. The differential scanning calorimeter of claim 26, further comprising means for calculating a total heat capacity.

32. The differential scanning calorimeter of claim 26, comprising means for calculating the apparent heat capacity for the sample and for the reference using:

$$C_{sa} = \frac{\tilde{q}_s}{\omega \cdot \tilde{T}_{ps}} \text{ and } C_{ra} = \frac{\tilde{q}_r}{\omega \cdot \tilde{T}_{pr}}.$$

33. The differential scanning calorimeter of claim 26, comprising means for calculating the nonreversing heat flow to the sample pan and the nonreversing heat flow to the reference pan using:

$$q_{sn} = \overline{q}_s - C_{sa} \cdot \frac{d\overline{T}_{ps}}{d\tau} \quad q_{rn} = \overline{q}_r - C_{ra} \cdot \frac{d\overline{T}_{pr}}{d\tau}.$$

34. The differential scanning calorimeter of claim 26, comprising means for calculating the differential reversing heat capacity of the sample from:

$$C_{prev} = C_{sa} - \frac{m_{ps}}{m_{ps}} \cdot C_{ra}.$$

35. The differential scanning calorimeter of claim 26, further comprising means for calculating a differential reversing heat flow, a differential nonreversing heat flow and a total heat flow using:

$$q_{rev} = C_{prev} \cdot \frac{d\overline{T}_{ps}}{d\tau}$$

$$q_{non} = q_{sn} - q_{rn}$$

$$q_{tot} = q_{rev} + q_{non}.$$

36. The differential scanning calorimeter of claim 26, further comprising means for calculating a differential nonreversing heat capacity from:

$$C_{pnon} = \frac{q_{non}}{\frac{d\overline{T}_{ps}}{d\tau}}$$

and means for calculating the differential total heat capacity from:

$$C_p = C_{prev} + C_{pnon}.$$

37. A method for calculating the reversing heat capacity of a sample from data obtained using a modulated differential scanning calorimeter comprising a differential scanning calorimeter cell having an independent sample measuring section and an independent reference measuring section comprising:

(a) varying a temperature of the differential scanning calorimeter cell according to a temperature program characterized by a periodic component superimposed upon a linear ramp;

(b) measuring a temperature of a sample pan in the sample measuring section and a temperature of a reference pan in the reference measuring section (c) measuring a heat flow to the sample and sample pan and a heat flow to the reference pan;

(d) deconvoluting the temperature of the sample pan and the temperature of the reference pan to obtain an amplitude of the temperature of the sample pan and an amplitude of the temperature of the reference pan;

(e) deconvoluting the heat flow to the sample and sample pan and the heat flow to the reference pan to obtain an amplitude of the heat flow to the sample and sample pan and an amplitude of the heat flow to the reference pan;

(f) calculating an apparent heat capacity for the sample;

(g) calculating a nonreversing heat flow to the sample and sample pan and to the reference pan; and (h) calculating a differential reversing heat capacity of the sample.

38. A differential scanning calorimeter having a DSC cell comprising:

(a) an absolute temperature detector for measuring a temperature of a base position on a sensor;

(b) a first differential temperature detector for measuring a temperature difference between a sample position and the base position, said sample position having a sample and a sample pan thereon;

(c) a second differential temperature detector for measuring a temperature difference between a reference position and the sample position, said reference position having a reference pan thereon;

(d) means for varying a temperature of the DSC cell according to a temperature program characterized as having a periodic modulation superimposed on a linear ramp;

(e) means for measuring a signal representative of heat flow to the sample and sample pan and means for measuring a signal representative of heat flow to the reference pan as the temperature of the DSC cell is varied according to the temperature program;

(f) means for deconvoluting the signal representative of heat flow to the sample and sample pan, means for deconvoluting the signal representative of heat flow to the reference pan, means for deconvoluting a signal representative of the temperature of the sample pan, and means for deconvoluting a signal representative of the temperature of the reference pan; and (g) means for calculating a differential reversing heat capacity.

* * * * *